(12) United States Patent
Rannard et al.

(10) Patent No.: US 10,675,251 B2
(45) Date of Patent: Jun. 9, 2020

(54) PARTICLES CONTAINING BRANCHED POLYMERS

(71) Applicant: The University of Liverpool, Liverpool (GB)

(72) Inventors: Steve Rannard, Liverpool (GB); Jane Ford, Liverpool (GB); Hannah Rogers, Liverpool (GB); Pierre Chambon, Liverpool (GB); Marco Giardiello, Liverpool (GB); Andrew Owen, Liverpool (GB); Neil Kitteringham, Liverpool (GB)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 0 days.

(21) Appl. No.: 15/326,775

(22) PCT Filed: Jul. 17, 2015

(86) PCT No.: PCT/GB2015/052089
§ 371 (c)(1),
(2) Date: Jan. 17, 2017

(87) PCT Pub. No.: WO2016/009227
PCT Pub. Date: Jan. 21, 2016

(65) Prior Publication Data
US 2017/0202781 A1      Jul. 20, 2017

(30) Foreign Application Priority Data
Jul. 18, 2014    (GB) .................................. 1412841.7

(51) Int. Cl.
| | |
|---|---|
| *A61K 9/51* | (2006.01) |
| *C08G 83/00* | (2006.01) |
| *C08F 220/20* | (2006.01) |
| *C08G 63/08* | (2006.01) |
| *C08F 2/38* | (2006.01) |
| *C08L 33/10* | (2006.01) |
| *A61K 31/513* | (2006.01) |

(Continued)

(52) U.S. Cl.
CPC .......... *A61K 9/5146* (2013.01); *A61K 9/5138* (2013.01); *A61K 9/5153* (2013.01);
(Continued)

(58) Field of Classification Search
None
See application file for complete search history.

(56) References Cited

U.S. PATENT DOCUMENTS

| | | | |
|---|---|---|---|
| 5,118,528 A | 6/1992 | Fessi et al. | |
| 5,462,829 A * | 10/1995 | Tyagi ................. | G03G 9/08755 430/109.3 |

(Continued)

FOREIGN PATENT DOCUMENTS

| | | |
|---|---|---|
| WO | 2009122220 A1 | 10/2009 |
| WO | WO2014/199175 * | 12/2014 |

OTHER PUBLICATIONS

Hatton (Hyperbranched Polydendrons: A new Macromolecular Architecture, Thesis, May 2014).*
(Continued)

*Primary Examiner* — Bong-Sook Baek
(74) *Attorney, Agent, or Firm* — Fox Rothschild LLP

(57) ABSTRACT

Particles comprising a branched polymer and either a block copolymer or a linear dendritic hybrid represent a category of useful materials. They may be used in for example drug delivery applications. They may be prepared by a method comprising the steps of: dissolving the branched polymer and block copolymer or linear dendritic hybrid, and optionally other component(s), in a solvent to form a solution; adding said solution to a different liquid; and removing said solvent to form a dispersion of co-precipitated particles.

12 Claims, 17 Drawing Sheets

Architecture of assembled NPs

(51) Int. Cl.
*A61K 31/536* (2006.01)
*C08G 81/02* (2006.01)
*C08F 220/34* (2006.01)
*C08F 222/10* (2006.01)
*C08F 220/18* (2006.01)
*A61K 31/192* (2006.01)
*A61K 31/4745* (2006.01)
*A61K 31/427* (2006.01)

(52) U.S. Cl.
CPC .......... *A61K 9/5192* (2013.01); *A61K 31/192* (2013.01); *A61K 31/427* (2013.01); *A61K 31/4745* (2013.01); *A61K 31/513* (2013.01); *A61K 31/536* (2013.01); *C08F 2/38* (2013.01); *C08F 220/20* (2013.01); *C08G 63/08* (2013.01); *C08G 81/025* (2013.01); *C08G 83/003* (2013.01); *C08L 33/10* (2013.01); *C08F 220/34* (2013.01); *C08F 2220/1825* (2013.01); *C08F 2222/1013* (2013.01); *C08F 2438/01* (2013.01)

(56) References Cited

U.S. PATENT DOCUMENTS

2008/0226739 A1* 9/2008 Wood .................... C12N 15/88
514/1.1

2011/0172314 A1* 7/2011 Findlay ................ B01F 17/005
514/772.6

OTHER PUBLICATIONS

Smeets (European Polymer Journal, 49 (9): 2528-2544, Sep. 2013).*
Qiu et al. Pharmaceutical Research, vol. 23, No. 1, Jan. 2006.*
Ford et al., "Multiple and Co-Nanoprecipitation Studies of Branched Hydrophobic Copolymers and A-B Amphiphilic Black Copolymers, Allowing Rapid Formation of Sterically Stabilized Nanoparticles in Aqueous Media," Macromolecules (Mar. 12, 2015); 48(6):1883-1893.
Frauenrath et al., "Dendronized Polymers—building a new bridge from molecules to nanoscopic objects," Progress in Polymer Science (2005); 30(3-4):325-384.
He et al., "Polymer Nanoparticles: Shape-Directed Monomer-to-Particle Synthesis," Journal of American Chemical Society (Feb. 4, 2009); 131(4):1495-1501.
Jie et al., "Micelle-like nanoparticles of star-branched PEO-PLA copolymers as chemotherapeutic carrier," Journal of Controlled Release (Dec. 10, 2005); 110(1):20-33.
Pojjak et al., "Preparation of Stable Electroneutral Nanoparticles of Sodium Dodecyl Sulfate and Brached Poly (ethylenimine) in the Presence of Pluronic F108 Copolymer," Langmuir (Nov. 22, 2011); 27(24):14797-14806.
Slater et al., "Architecture-driven aqueous stability of hydrophobic, branced polymer nanoparticles prepared by rapid nanoprecipitation," Soft Matter (Jan. 1, 2012); 8(30):9816-9827.

* cited by examiner

Architecture of assembled NPs

CNP of EBiB tBuMA-EGDMA + linear dendritic polymers
90:10

| | G2-M tBuMA | | | EBiB DEAEMA | | | G2-M DEAEMA | | |
|---|---|---|---|---|---|---|---|---|---|
| pH | $D_z$ (nm)[a] | PDI | $\zeta$ (mV)[b] | $D_z$ (nm)[a] | PDI | $\zeta$ (mV)[b] | $D_z$ (nm)[a] | PDI | $\zeta$ (mV)[b] |
| 2 | 196.4 | 0.135 | +40.5 | - | - | - | - | - | - |
| 4 | 161.0 | 0.114 | +45.6 | - | - | - | - | - | - |
| 7.8 | - | - | - | 191.5 | 0.109 | +39.6 | 234.2 | 0.051 | +76.6 |
| 12 | 213.6 | 0.224 | -63.7 | 252.1 | 0.269 | -43.4 | 212.3 | 0.138 | -60.4 |

EBiB tBuMA-EGDMA

[a] All diameters are given as z-average values as measured by dynamic light scattering.
[b] All zeta potentials are given as surface charge values as measured by dynamic light scattering.

Fig. 14

CNP of EBiB fBuMA-EGDMA + linear dendritic polymers
90:10

|  | G0-M DEAEMA | | | | G1-M DEAEMA | | | | G2-M DEAEMA | | | |
|---|---|---|---|---|---|---|---|---|---|---|---|---|
| pH | $D_z$(nm)[a] | PDI | $\zeta$ (mV)[b] | | $D_z$ (nm)[a] | PDI | $\zeta$ (mV)[b] | | $D_z$ (nm)[a] | PDI | $\zeta$ (mV)[b] | |
| 2 | – | – | – | | – | – | – | | – | – | – | |
| 4 | – | – | – | | – | – | – | | 234.2 | 0.051 | +76.6 | |
| 7.8 | 201.3 | 0.191 | | | 195.2 | 0.168 | | | 212.3 | 0.138 | −60.4 | |
| 12 | | | | | | | | | | | | |

EBiB fBuMA-EGDMA

[a] All diameters are given as z-average values as measured by dynamic light scattering.
[b] All zeta potentials are given as surface charge values as measured by dynamic light scattering.

Fig. 15

CNP of EBiB DEAEMA-EGDMA + linear dendritic polymers 90:10

| | | G2-M DEAEMA | | | G2-M HPMA | | |
|---|---|---|---|---|---|---|---|
| pH | $D_z$ (nm)[a] | PDI | ζ (mV)[b] | $D_z$ (nm)[a] | PDI | ζ (mV)[b] | |
| 4 | | | | 52.17 | 0.096 | +35.9 | |
| 7.8 | 83.19 | 0.146 | +27.6 | 77.33 | 0.210 | +38.3 | |

EBiB DEAEMA-EGDMA

[a] All diameters are given as z-average values as measured by dynamic light scattering.
[b] All zeta potentials are given as surface charge values as measured by dynamic light scattering.

CNP of EBiB HPMA-EGDMA + linear dendritic polymers 90:10
G2-M DEAEMA
| pH | $D_z(nm)^a$ | PDI | $\zeta\ (mV)^b$ |
|---|---|---|---|
| 4 | 149.1 | 0.066 | +45.4 |
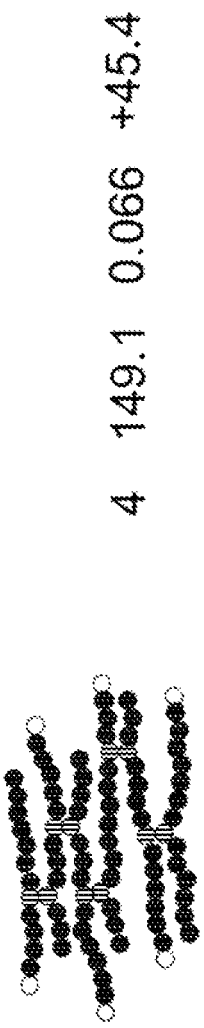
EBiB HPMA-EGDMA
*a* All diameters are given as z-average values as measured by dynamic light scattering.
*b* All zeta potentials are given as surface charge values as measured by dynamic light scattering.
Fig. 18

PARTICLES CONTAINING BRANCHED POLYMERS

This application is the U.S. National Phase of International Patent Application No. PCT/GB2015/052089, filed Jul. 17, 2015, which claims priority to GB Application No. 1412841.7, filed Jul. 18, 2014, the disclosures of which are incorporated herein by reference in their entirety.

The present invention relates to particles comprising organic polymers. These particles are useful in for example drug delivery applications.

We have previously disclosed various polymeric materials and technologies to produce molecular architectures which are useful in various fields including biology and nanotechnology.

For example WO 2009/12220 discloses polymer-dendrimer hybrids, also known as polydendrons, which comprise a branched vinyl polymer scaffold carrying dendrons: these polydendrons possess advantageous dendrimer-type properties in part due to their multiply branched nature, without the disadvantages of complex conventional dendrimer processes.

It is useful to be able to control the properties of such materials including for example their size, size distribution, functionality, hydrophobicity/hydrophilicity, and behaviour in systems of use, e.g. in aqueous systems in the case of biological applications.

We have now developed a new category of useful materials.

From a first aspect the present invention provides particles comprising a branched polymer and either a block copolymer or a linear dendritic hybrid.

The branched polymer may be of various types. Two example types are branched vinyl polymers and branched polyesters.

Branched vinyl polymers may be prepared by known methods, from monofunctional vinyl monomers and difunctional vinyl monomers (branching agents).

Branched polyesters may be prepared by for example ring opening polymerization of monofunctional lactone monomers and difunctional lactone monomers (branching agents).

Block copolymers comprise blocks or segments each of which have repeating units of the same type within each block and which are different between block segments. The present invention has been found to be particularly effective with diblock copolymers, i.e. copolymers which have two distinct blocks. Other block copolymers may be used, e.g. triblock copolymers.

Linear dendritic hybrids, also known as linear dendritic polymers, likewise comprise distinct segments, one of which is a linear polymer chain and another of which is a dendron. We have found that the present invention is particularly effective with a linear dendritic hybrid which comprises a homopolymer terminating in or initiated by a dendron. Nevertheless other types of linear dendritic hybrid (e.g. wherein the linear polymer is itself a copolymer, for example a statistical copolymer, block copolymer or diblock copolymer) may be used in the present invention. Thus for example a linear dendritic hybrid may comprise one block joined to another block which is then joined to a dendron.

The particles may be nanoparticles, for example particles wherein at least one dimension, or wherein the z-average diameter (also referred to as the average hydrodynamic diameter), is no greater than about 1000 nm. The particles may have z-average diameters less than 800 nm, or less than 500 nm, or less than 300 nm, e.g. around 50 to 300 nm, or 50 to 250 nm, or 100 to 200 nm.

It is important to note that the particles of the present invention contain two types of polymeric material, i.e. a branched polymer and either a block copolymer or a linear dendritic hybrid (and optionally further materials as discussed below) but that these are not covalently bonded to each other. In contrast, polydendrons, as disclosed in for example WO 2009/12220, contain dendron units which are covalently attached to a branched vinyl polymer scaffold. In the present invention, the different polymeric materials are associated with each other within a particle structure, but are not covalently bonded to each other. Preferably most, or substantially all, or all, of the particles have the same general structure. The regular way in which the parts associate, intermingle or assemble brings about reliable and reproducible properties.

The combination of polymeric structures in the present invention brings about particular advantages.

The first essential component, the branched polymer component, may be generally hydrophobic and therefore useful for providing an environment for associating with, carrying, or encapsulating, a hydrophobic compound, moiety or payload, for example a drug. Alternatively it may have hydrophilic properties. It may be responsive to pH or other conditions or stimuli such that its properties, e.g. its hydrophobic/hydrophilic properties, its structure, and/or its behaviour in liquid phases, may vary depending on the environment.

The second essential component has at least two segments (different homopolymer or copolymer blocks in the case of block copolymers, or a linear polymer block plus a dendron in the case of linear dendritic hybrids). This allows the resultant particles to be suitable for or tailorable for use in a variety of media and environments and for a variety of applications. It also allows one of the segments to act as a stabilizer to stabilize the particles within liquid media, for example in aqueous media, and optionally to provide salt stability to stabilize the particles in a range of salt conditions and/or in a range of physiological conditions which might be encountered in living systems.

The block copolymer or linear dendritic hybrid may comprise a hydrophobic segment. This enables it to associate with a hydrophobic branched polymer (and optionally with hydrophobic carried material). The hydrophobic segment may comprise a vinyl polymer.

The block copolymer or linear dendritic hybrid may comprise a hydrophilic segment. This is useful in for example aqueous environments and enables the stabilisation of the nanoparticles. The hydrophilic segment may comprise a polyether structure such as polyethylene glycol (PEG) or PEO, for example.

Of course, the block copolymer or linear dendritic hybrid may comprise both a hydrophobic segment and a hydrophilic segment and thereby exhibit amphiphilic behaviour.

Thus we have developed particularly advantageous combinations where the branched polymer is hydrophobic and forms a hydrophobic core and where the block copolymer or linear dendritic hybrid is amphiphilic such that one segment thereof can associate with the hydrophobic core and another segment thereof can stabilise the particles in aqueous media. These exhibit considerable uniformity in terms of size, and stability in aqueous media and under varied salt conditions.

Nevertheless other combinations of types of polymer and consequent properties are also useful in other scenarios, and are within the scope of the present invention.

The branched polymer, block copolymer or linear dendritic hybrid may comprise chemistry which is responsive to pH or other conditions or stimuli such that its properties, e.g. its hydrophobic/hydrophilic properties, may vary depending on the environment.

The linear dendritic hybrid comprises a linear polymer chain and a dendron. Said linear polymer chain may itself be a copolymer, e.g. a statistical copolymer or a block copolymer.

The particles may comprise a further material, for example a chemical compound, organic compound, hydrophobic compound, hydrophilic compound, drug, prodrug or therapeutically, diagnostically or biologically useful material. Indeed, one of the main uses of the present invention is in drug delivery.

The further materials, e.g. drugs or biologically active materials, may be included as or within separate compounds within the particles, or may be covalently bound to one of the polymeric structures, e.g. to the branched polymer, block copolymer or linear dendritic hybrid From a further aspect the particles are prepared by co-precipitation.

The method of preparation may comprise:
dissolving the branched polymer and either block copolymer or linear dendritic hybrid, and optionally other component(s), in a solvent to form a solution
adding said solution to a different liquid
removing the solvent, to form a dispersion of co-precipitated particles within the liquid.

The solvent may be removed by for example allowing said solvent to evaporate or through dialysis.

The dispersion may be used for applications, e.g. therapeutic applications, as it is, or alternatively the dispersion may be concentrated or gelled, or the liquid may be removed to result in solid particles.

The solvent in which the materials are dissolved may be an organic solvent, suitably a solvent which is miscible with the liquid in which precipitation occurs, e.g. water-miscible solvents. For example the solvent in which the materials are dissolved may be e.g. acetone, acetonitrile, dimethyl formamide, dimethyl sulfoxide, dioxane, ethanol, isopropyl alcohol, methanol, tetrahydrofuran and any combination and mixture of them or combinations comprising water.

The solvent in which the materials are dissolved may be one which is chosen because it evaporates relatively easily, e.g. one which has a boiling point of 80 degrees C. or less, or 70 degrees C. or less, or 60 degrees C. or less.

The liquid in which the precipitation occurs may for example be water or other aqueous system, or other liquid in which the materials do not dissolve, or dissolve less well in comparison to the first solvent.

Various aqueous solutions can be used. Some examples include:
aqueous solutions of for example alkali metal/halogen salts (e.g. NaCl, LiBr, KCl). at all concentrations (up to saturation)
aqueous solution within a pH range of 0 to 12, including acid and base (BrØnsted-Lowry mineral and organic acids and bases) solutions (e.g. aqueous solutions of e.g. HCl, H$_2$SO$_4$, acetic acid, NaOH, or KOH)
surfactant (e.g. Sodium dodecyl sulphate, amphiphilic diblock copolymers, TWEEN®, BRIJ®) solutions in water at all concentrations (below and above critical micellar concentration)
biological media [e.g. transport buffer, bovine serum albumin (BSA), dulbecco's modified eagle's medium (DMEM), Roswell park memorial institute 1640 (RPMI 1640), foetal bovine serum (FBS)] in aqueous systems, and mixtures of the same, at all suitable concentrations.

The aqueous systems listed above provide some indication of the wide range of systems in which the present invention works, consistent with applications in a variety of conditions including therapeutic applications, where there is a need to endure varied and sometimes extreme physiological environments.

The liquid in which precipitation occurs may be a mixture of water and organic solvent e.g. acetone/water mixture, THF/water, MeOH/water, EtOH/water, or IPA/water. The amount of water in such mixtures may optionally be 2 parts water by volume to 1 part organic solvent by volume, or greater than 2 parts water (e.g. greater than 3 parts water, e.g. greater than 4 parts water) by volume to 1 part organic solvent by volume.

One of the inventive points of distinction of the present invention over the prior art is that the present invention involves the co-precipitation of two specific types of polymer at the same time from organic solvent into water. Whereas precipitation (including nanoprecipitation) of organic polymers has previously been disclosed in various documents and has been carried out with varying degrees of success (see, for example, Slater et al, *Soft Matter* 2012, 8, 9816-9827), this has not been in relation to a combination of polymer types as defined in the present invention. We are first to recognize, and demonstrate, the benefits of such co-precipitation.

Optionally, the co-precipitation may be carried out multiple times. Thus, after the formation of a dispersion of co-precipitated particles within the liquid (and the subsequent removal of organic solvent), the following method steps may additionally be carried out, one or more times:
adding further solution (of the branched polymer and either the block copolymer or the linear dendritic hybrid, and optionally the other component(s), in the solvent) to the liquid
removing the solvent.

We have found that, by carrying out multiple co-precipitation, it is possible to increase the concentration of particles within the liquid whilst substantially maintaining the particle size, PdI and stability. In other words, multiple nanoprecipitation can be used to provide more of the same type of nanoparticles per unit volume, whereas it might have been expected that multiple nanoprecipitation would result in significantly larger particles, different dispersity characteristics, or instability. This is particularly advantageous in facilitating drug delivery where an enhanced payload can result in practical therapeutic advantages and cost benefits.

The Branched Polymer Component

The branched polymer is an essential component of the particles of the present invention.

The branched polymer is non-gelled and processable and optionally of low viscosity. It is soluble in organic solvents, as described above in relation to a suitable method of forming the particles by precipitation from such solvents into a different medium. It can be contrasted with polymer structures which are insoluble and/or exhibit high viscosity, such as extensively crosslinked insoluble polymer networks, high molecular weight linear polymers, or microgels.

Branched Vinyl Polymers

The branched polymer may be a branched vinyl polymer. This can be made by, but is not limited to being made by, living polymerization, controlled polymerization or conventional chain-growth polymerization techniques such as free radical polymerisation. Several types of living and controlled polymerization are known in the art and suitable for use in the present invention. A preferred type of living polymerization is Atom Transfer Radical Polymerization (ATRP); however other techniques such as Reversible Addition-Fragmentation chain-Transfer (RAFT) and Nitroxide Mediated Polymerisation (NMP) or conventional free-radical polymerization controlled by the deliberate addition of chain-transfer agents are also suitable syntheses.

The skilled person is aware of techniques to provide branched but non-gelled vinyl polymers. For example, suitable procedures are described in N. O'Brien, A. McKee, D. C. Sherrington, A. T. Slark and A. Titterton, *Polymer* 2000, 41, 6027-6031; T. He, D. J. Adams, M. F. Butler, C. T. Yeoh, A. I. Cooper and S. P. Rannard, *Angew. Chem. Int. Ed.* 2007, 46, 9243-9247; V. Bütün, I. Bannister, N. C. Billingham, D. C. Sherrington and S. P. Armes, *Macromolecules* 2005, 38, 4977-4982; I. Bannister, N. C. Billingham, S. P. Armes, S. P. Rannard and P. Findlay, *Macromolecules* 2006, 39, 7483-7492; and R. A. Slater, T. O McDonald, D. J. Adams, E. R. Draper, J. V. M. Weaver and S. P. Rannard, *Soft Matter* 2012, 8, 9816-9827. The non-gelled and soluble products of the present invention are different to materials disclosed in L. A. Connal, R. Vestberg, C J. Hawker and G. G. Qiao, *Macromolecules* 2007, 40, 7855-7863 which are known to comprise multiple cross-linking in a gelled network.

The polymerization of each vinyl polymer chain starts at an initiator. Polymerization of monofunctional vinyl monomers leads to linear polymer chains. Copolymerization with difunctional vinyl monomers leads to branching between the chains. In order to control branching and prevent gelation there should be less than one effective brancher (difunctional vinyl monomer) per chain. Under certain conditions, this can be achieved by using a molar ratio of brancher to initiator of less than one: this assumes that the monomer (i.e. the monofunctional vinyl monomer) and the brancher (i.e. the difunctional vinyl monomer) have the same reactivity, that there is no intramolecular reaction, that the two functionalities of the brancher have the same or similar reactivity, and that reactivity remains the same even after part-reaction. Of course, the systems and conditions may be different, but the skilled person understands how to control the reaction and determine without undue experimentation how a non-gelled structure may be achieved. For example, under dilute conditions some branchers form intramolecular cycles which limit the number of branchers that branch between chains even if the molar ratio of brancher to initiator (i.e. polymer chain) is higher than 1:1 in the reaction.

Initiators and other reagents used in the polymerisation process are as known in the art. For example, in ATRP, convenient and effective initiators include alkyl halides (e.g. alkyl bromides) and in conventional free radical polymerisation, effective initiators include azo compounds Other Branched Polymers Other suitable types of branched polymers include branched polyesters. These may be prepared by for example ring opening polymerization of monofunctional lactone monomers and difunctional lactone monomers (branching agents). Ring opening polymerization methods and materials are known in the art, for example from Nguyen et al., *Polym Chem* 2014, 5, 2997-3008.

Amount of Branched Polymer in Relation to Linear Polymer and Other Optional Components The amount of branched polymer (e.g. branched vinyl polymer) may optionally be no greater than 95 wt %, or no greater than 75 wt %, or no greater than 50 wt %, or no greater than 10 wt %, or no greater than 1 wt %. In this context wt % denotes the amount of branched vinyl polymer as a percentage of the total mass of solid material in the particles. The amount of branched polymer may optionally be at least 0.1 wt %, or at least 0.5 wt %. For example the amount of branched polymer may be between about 0.1 wt % and 95 wt %, e.g. between 1 wt % and 10 wt %.

Surprisingly we have found that relatively low amounts of branched polymer (optionally around 1-10 wt % in some cases) are effective in being able to direct the nanoprecipitation, and in allowing the formation of regular particles of narrow dispersity. Thus, in some applications this can bring a benefit in allowing the amount of other component(s) (i.e. the block copolymer component or the linear dendritic hybrid, plus any other components e.g. carried materials) to be maximised.

The Block Copolymer Component

The block copolymer component can comprise various types of polymer including for example vinyl polymers, polyethers (e.g. PEO or PPO), polyesters (e.g. polycaprolactone or polylactic acid), polyurethanes, polyamides, or polycarbonates. There are (at least) two distinct blocks. The type of polymer forming each block may be the same or different, though of course if the type of polymer is the same then for the blocks to differ the monomers, or mixture of monomers, must differ.

For example, the block copolymer may comprise two blocks each of which is a vinyl polymer chain, wherein the vinyl monomer making up one block differs from the vinyl monomer making up the other block.

Alternatively the type of polymer forming each block may be different. For example the block copolymer may comprise one block which is a vinyl polymer chain and a second block which is a polyether chain or a polyester chain.

One convenient known way of preparing a block copolymer wherein one block is a vinyl chain is to use a macroinitiator in a vinyl polymerisation process wherein the macroinitiator comprises the other or another block. For example, the macroinitiator may be a bromide initiator comprising a PEO or other polymer chain. In a further variation, said initiator may be bifunctional and may therefore allow the preparation of a triblock copolymer (for example being an A-B-A block copolymer where A is a vinyl, often hydrophobic, block, and B is a PEO, hydrophilic, block).

The molecular mass of the PEO may for example be greater than 1,000 g/mol, for example between 1,000 and 10,000 g/mol; for example PEG 2K or PEG 5K.

Another example is to use a polymer (e.g. a hydrophilic polymer) bearing a hydroxyl group as a macroinitiator for ring opening polymerisation (e.g. of cyclic esters, e.g. ε-caprolactone or other cyclic structures). Known ring-opening polymerisation techniques may be used.

Other ways to synthesise diblock copolymers include for example one-pot methods in which one monomer (e.g. a vinyl monomer) is polymerised first (generally a hydrophilic block first, but not necessarily) and then, when this first reaction has reached the desired monomer conversion, and without any purification of the first block, the second monomer (which may for example lead to a hydrophobic block if the first monomer leads to a hydrophilic block) may be added in situ. In each case, the monomers added may be a mixture of monomers leading to a statistical copolymerisation within each block.

Other known methods of preparing block copolymers may be used.

The Linear Dendritic Hybrid

The linear dendritic hybrid comprises a polymer chain and a dendron. The dendron is covalently attached to the polymer chain. The polymer chain can comprise various types of polymer including vinyl polymers, polyesters, polyamides, polycarbonates, polyurethanes, or polyethers (e.g. PEO or PPO).

Linear dendritic hybrids are known from various documents, e.g. F. Wurm, H. Frey, *Prog. Polym. Sci.* 2011, 36, 1-52.

The dendron may be incorporated in various ways. One possible method uses dendrons as macromolecular initiators in for example vinyl polymerisation. This allows the formation of for example linear dendritic hybrids having a vinyl polymer chain with a dendron at the end of the chain. Dendrons may also be used as chain transfer agents to regulate and initiate a chain growth polymerisation.

In order to be able to initiate polymerization, the dendrons must bear suitable reactive functionality. For example, in ATRP, dendrons which carry halides (e.g. bromides) at their focal points can act as initiators. In this scenario, propagation starts at the apex, or focal point, of the dendron "wedge". The skilled person is well aware of the types of components and reagents which are used in polymerisations including ATRP and other living or controlled polymerizations and conventional free radical polymerisation, and hence the type of functionality which must be present on or introduced to dendrons for them to act as initiators or chain transfer agents.

For example, one possible way of introducing bromo groups to dendrons is to functionalize dendron alcohols with alpha-bromoisobutyryl bromide. There are however many other ways of functionalizing dendrons so that they can act as initiators and chain transfer agents, and other types of functionality which will initiate polymerization. The concept of a dendron initiator is applicable to all suitable types of polymerization and the functionality can be varied as necessary.

Another method of incorporating dendron comprises ring opening polymerisation e.g. of cyclic esters, using dendrons with suitable functional groups (e.g. —OH groups).

A further method uses dendrons as chain transfer agents for polymerisation with reversible addition-fragmentation chain transfer (RAFT) or conventional free radical polymerisation.

Other possible methods include post-functionalisation of polymers via chain-end/dendron coupling, for example through the use of a thiol group at the focal point.

Other methods known in the art for the incorporation of dendrons into linear dendritic hybrids may be used.

There is no particular limitation regarding the type of dendron that can be used, or the chemistry used to prepare the dendrons. In some scenarios it is desirable to have particular groups present at the surface (i.e. at the tips of the "branches" of the dendron), and these may be incorporated during the synthesis of the dendron. The dendrons are preferably non-vinyl.

Any suitable coupling chemistry may be used to build up the dendrons. In one example, amines and alcohols may be coupled together, for example using carbonyldiimidazole. This is, however, merely one example and numerous other coupling methods, such as Michael addition chemistry or well known esterification techniques, are possible.

The dendrons may comprise various moieties including for example amines (e.g. dendrons which are branched at tertiary amine centres, or dendrons which terminate at $NMe_2$ groups), hydroxyl groups, acids, carboxyl groups, or PEG groups.

The branched polymer may optionally contain alcohol groups.

The branched polymer may optionally contain amine groups.

The branched polymer may optionally contain carboxyl groups.

The block copolymer may optionally contain alcohol groups.

The block copolymer may optionally contain amine groups.

The block copolymer may optionally contain carboxyl groups.

The polymer chain of the linear dendritic hybrid may optionally contain alcohol groups.

The polymer chain of the linear dendritic hybrid may optionally contain amine groups.

The polymer chain of the linear dendritic hybrid may optionally contain carboxyl groups.

EXAMPLES, FIGURES AND EXPERIMENTAL DETAILS

The present invention will now be described in further non-limiting detail, by way of example, with reference to the figures in which:

FIGS. 14 to 18 show some combinations of branched polymers and linear dendritic hybrids and their properties;

PARTICLES CONTAINING BRANCHED POLYMERS AND BLOCK COPOLYMERS

One group of particles in accordance with the present invention are those which contain branched polymers and block copolymers.

Figure 1:
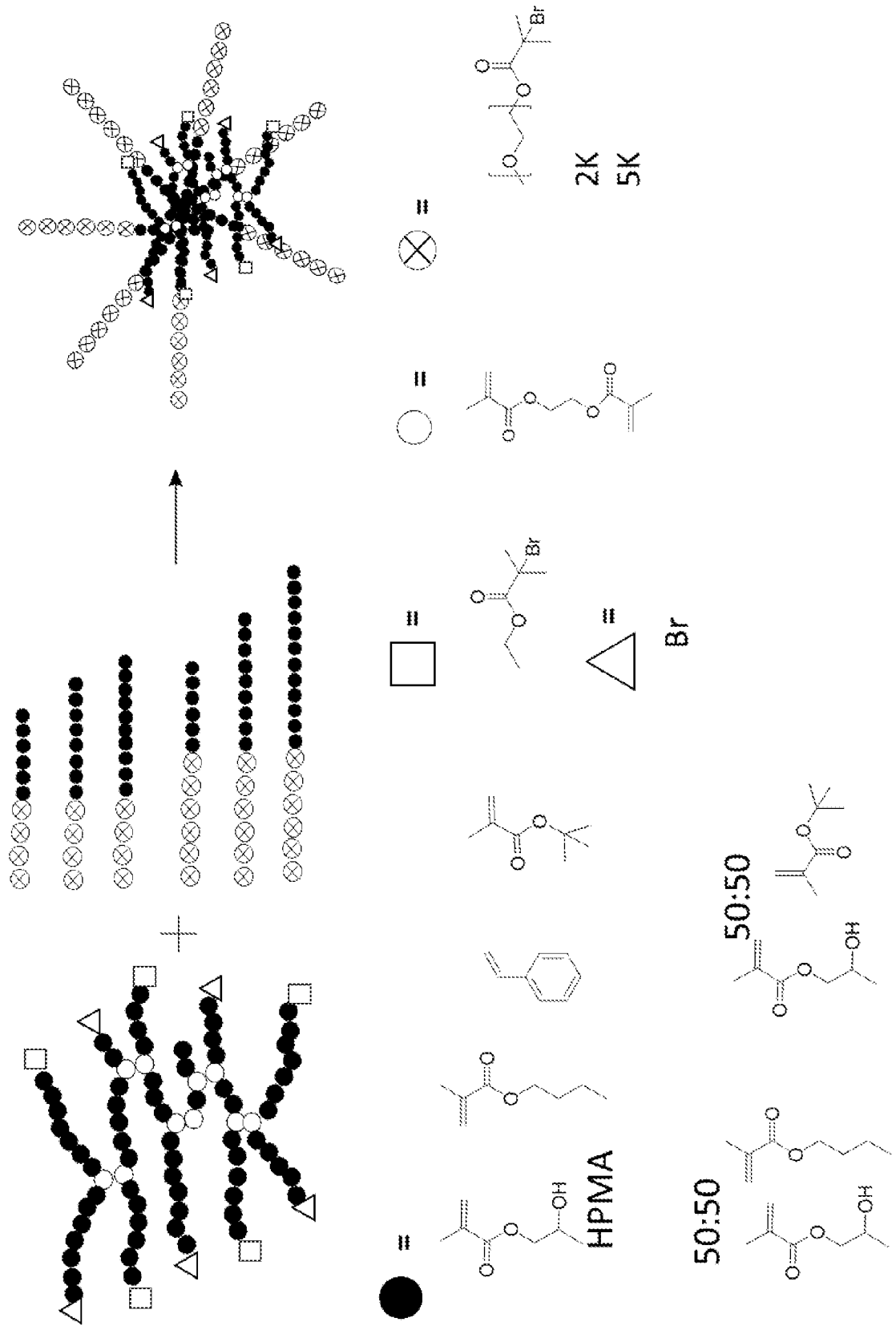
FIG. 1 shows a schematic representation of a branched vinyl polymer, diblock copolymers, and a particle of the present invention containing the branched vinyl polymer and diblock copolymers, and also some monomers which may be used in the preparation of the polymers.

FIG. 1 shows an overview of some components used. A branched vinyl polymer (top left) contains linear chains formed from vinyl monomers which are branched by use of a brancher. A wide variety of vinyl monomers may be used, some examples of which are shown (bottom left).

The vinyl monomers shown in the bottom left of FIG. 1, and their abbreviations as used herein, are as follows:

HPMA: hydroxypropyl methacrylate. 2-hydroxypropyl methacrylate is shown, though the invention can utilize not only this isomer alone but optionally a commercially available mixture of this isomer and 2-hydroxyisopropyl methacrylate or the latter alone.

nBuMA: n-butyl methacrylate

Styrene tBuMA: t-butyl methacrylate

DEAEMA: N,N-diethylaminoethyl methacrylate, a monomer which is hydrophilic in comparison to the above-mentioned monomers, and pH-responsive.

PEG 2K, and the other being $HPMA_{40}$, $HPMA_{80}$, or $HPMA_{120}$) in various ratios are shown in the following table:

|  | Branched polymer: diblock polymer | | | | | |
|---|---|---|---|---|---|---|
|  | PEG2K HPMA40 | PEG2K HPMA80 | PEG2K HPMA120 | PEG5K HPMA40 | PEG5K HPMA80 | PEG5K HPMA120 |
| 90/10 | | | | | | |
| Z-ave (d nm) | 113 | 114 | 120 | 111 | 112 | 132 |
| PDI | 0.067 | 0.045 | 0.066 | 0.055 | 0.045 | 0.059 |
| 80/20 | | | | | | |
| Z-ave (d nm) | 94 | 127 | 111 | 103 | 106 | 127 |
| PDI | 0.123 | 0.061 | 0.033 | 0.152 | 0.118 | 0.043 |
| 70/30 | | | | | | |
| Z-ave (d nm) | 106 | 115 | 108 | 121 | 106 | 113 |
| PDI | 0.029 | 0.053 | 0.037 | 0.061 | 0.124 | 0.069 |
| 60/40 | | | | | | |
| Z-ave (d nm) | 115 | 111 | 103 | 107 | 103 | 117 |
| PDI | 0.047 | 0.037 | 0.069 | 0.028 | 0.065 | 0.059 |
| 50/50 | | | | | | |
| Z-ave (d nm) | 167 | 124 | 226 | 154 | 141 | 135 |
| PDI | 0.024 | 0.055 | 0.035 | 0.048 | 0.063 | 0.051 |

As indicated in FIG. 1, combinations of monomers may be used e.g. HPMA and nBuMA, or HPMA and tBuMA.

Other materials used include the following, also shown in FIG. 1:

EBIB: ethyl alpha-bromoisobutyrate, an initiator commonly used to initiate polymerisation EGDMA: ethylene glycol dimethacrylate, a suitable brancher PEG 2K or PEG 5K: polyethylene oxide of size 2K or 5K (although of course other sizes are possible), which is bromo-functionalised so that it can act as a macroinitiator for vinyl polymerisation. Because of the number of ethylene oxide groups present in the polyethylene oxide (PEO), PEG 2K is also referred to as $PEO_{45}$ and PEG 5K is also referred to as $PEO_{114}$.

Other monomers, branchers, initiators and other materials can also be used including:

BDME, 1,4-butanediol di(methacryloyloxy)-ethyl ether, a pH responsive brancher

Diblock copolymers of varying lengths are shown (top middle): these can for example have one block formed from a vinyl monomer selected from those shown, e.g. HPMA, and a second block of different chemistry e.g. polyethylene oxide. One possible preparative procedure uses bromo-functionalised polyethylene oxide (e.g. PEG 2K or 5K) (FIG. 1, bottom right) as a macroinitiator for vinyl polymerisation. The resultant amphiphilic diblock copolymer can be co-precipitated with the branched vinyl polymer to form a particle which is schematically illustrated top right. In this example the hydrophilic polyethylene oxide chains of the block copolymer are shown on the outside of the particle, as would be the case in aqueous systems.

Figure 2:
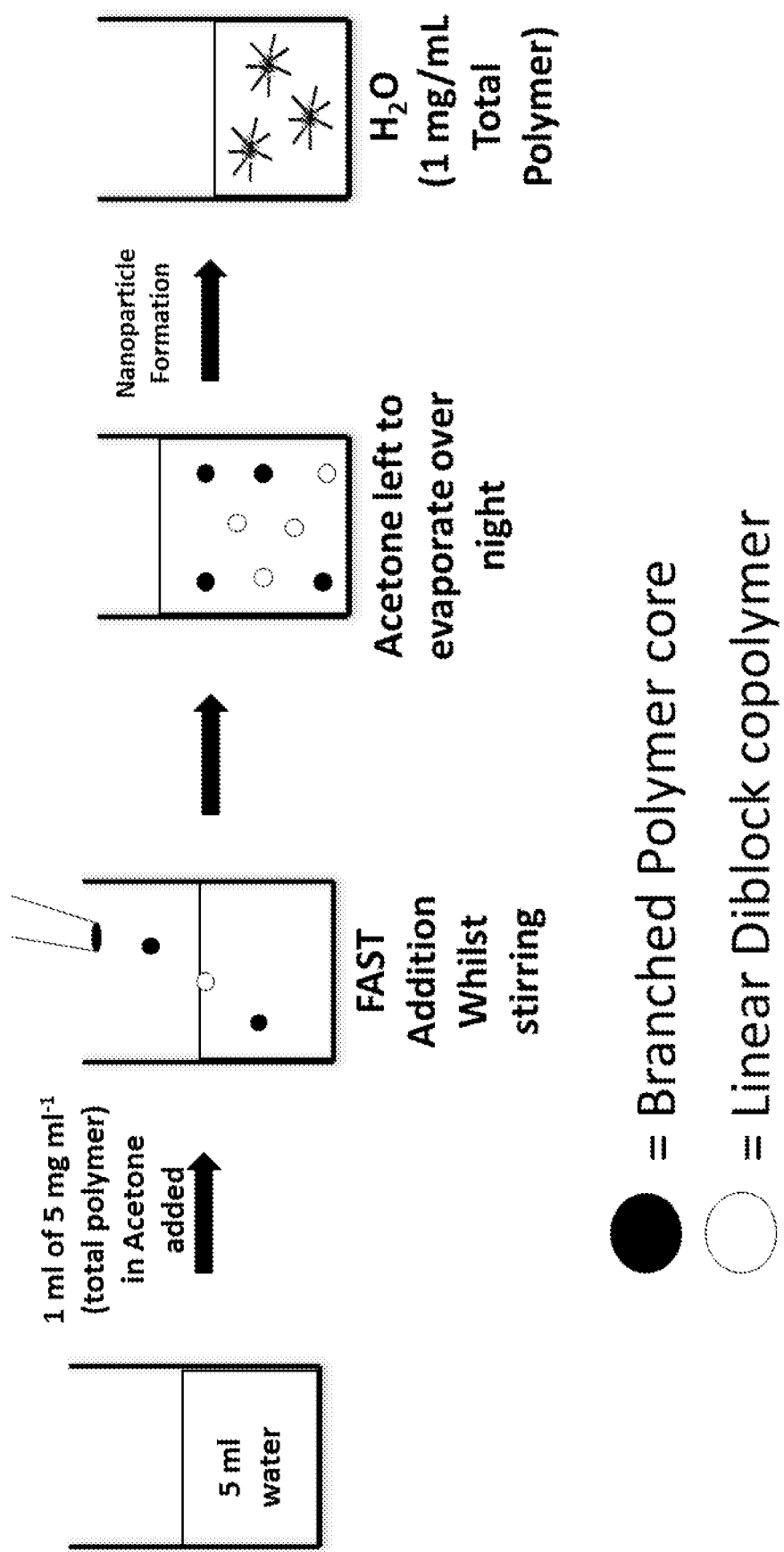
FIG. 2 shows a schematic representation of one possible co-precipitation procedure in accordance with the present invention.

As shown in FIG. 2, the co-precipitation may for example be carried out by adding both polymers, in suitable organic solvent, to water, and then allowing the organic solvent to evaporate.

Some examples of particle size (dynamic light scattering size) and polydisersity (PDI) values for co-precipitates of branched vinyl polymer (poly-HPMA-EGDMA) with amphiphilic diblock copolymer (one block being PEG 5K or It can be seen that, in these examples, the sizes (z-average diameters) of the co-nanoprecipitated particles range from 90 to 230 nm, and that there are narrow PDI values throughout showing their consistency and uniformity.

Figure 3:
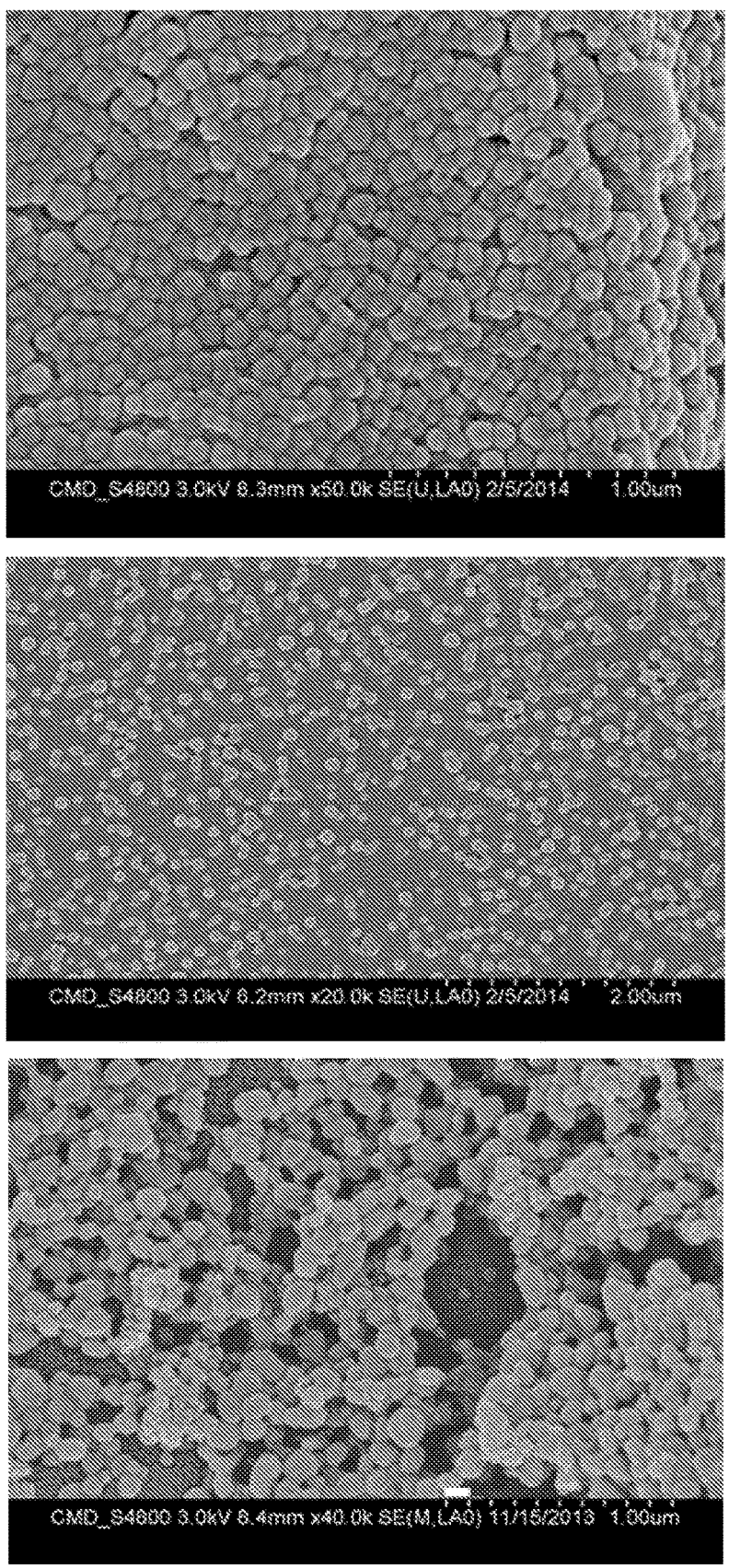
FIG. 3 shows SEM images of some nanoparticles in accordance with the present invention.

SEM shows the sizes and spherical nature of the nanoparticles. FIG. 3 shows some examples: co-precipitates of branched vinyl polymer (poly-HPMA-EGDMA) with PEG 5K-$HPMA_{120}$ in the ratios 80:20 (top) and 90:10 (middle) and with PEG 2K-$HPMA_{120}$ in the ratio 50:50 (bottom).

Figure 4:
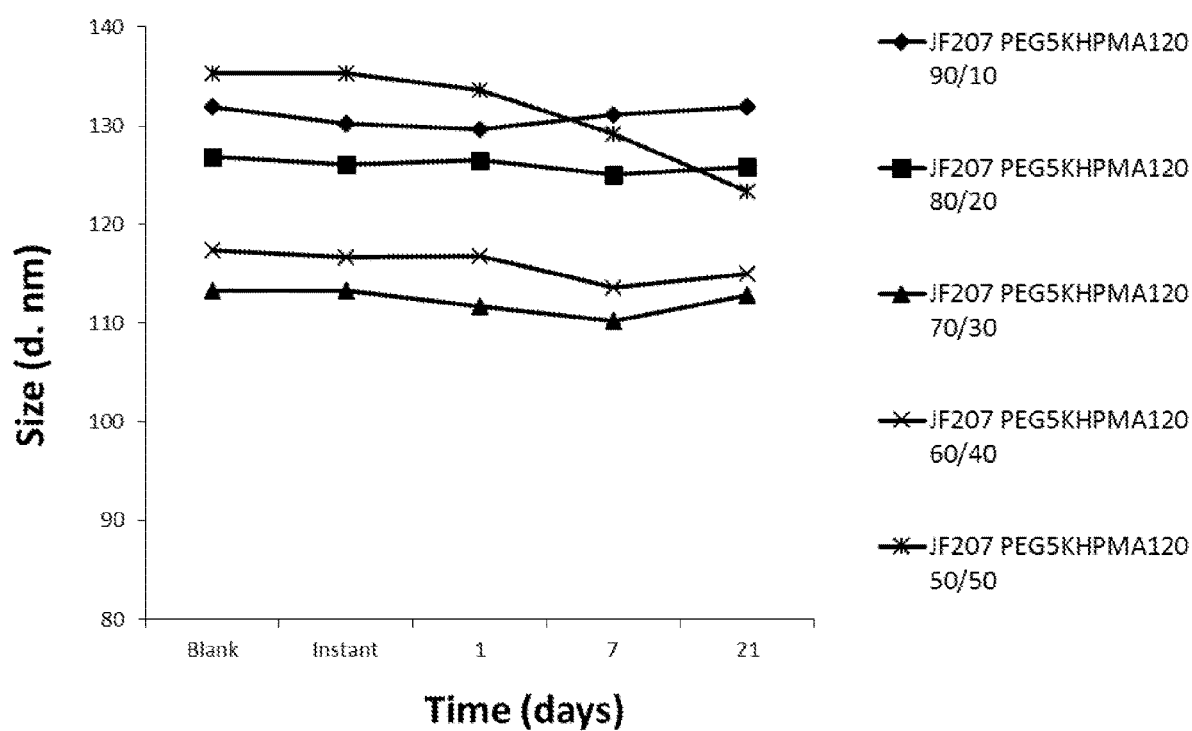
FIGS. 4 and 5 shows the stability of particles of the present invention to salt solution and over time.

FIG. 4 shows the stability of various particles to salt solution (0.5M NaCl). "Blank" denotes before salt is added, "Instant" immediately after, and 1, 7 and 21 the number of days afterwards. The particles exhibit considerable salt stability, which is important for use in physiological environments. Previous examples of particles formed solely from branched vinyl polymers alone have been shown to be unstable in the presence of salts (Slater et al, *Soft Matter* 2012, 8, 9816-9827).

The following example provides more details of some nanoparticles containing hydrophobic cores and amphiphilic diblock stabilisers:

Example 1: Nanoparticles Containing Branched Hydrophobic Core Polymer and Linear Amphiphilic Diblock Copolymer Preparation of Polymers ATRP was used for the synthesis of linear $PEO_{45}$-p($HPMA_{120}$) and the branched statistical copolymer of EGDMA and HPMA p($HPMA_{50}$-$EGDMA_{0.9}$). Polymers were analysed by triple detection gel permeation chromatography (GPC) and $^1H$ NMR. Monomer to polymer conversion was monitored by $^1H$ NMR using anisole as an internal reference.

The linear amphiphilic block copolymer was synthesised during a one step ATRP reaction in methanol at 30° C. For introduction of the hydrophilic block a $PEO_{45}$-Br macroinitiator (2 kDa) was added accordingly to HPMA along with the catalytic system Cu(I)Cl/2,2'-Bipyridine (Bpy) in the following ratio [Macroinitiator]:[Monomer]:[Cu(I)Cl]:[Bpy]=1:120:1:2. The targeted number average degree of polymerisation ($DP_{HPMA}$) was 120 HPMA monomer units and GPC confirmed a number average $DP_{HPMA}$=127 monomer units ($M_n$=20300 Da) with a narrow dispersity (Đ=1.23).

ration. The nanoparticle dispersions were analysed by dynamic light scattering (DLS) and scanning electron microscopy (SEM). The resulting z-average diameters (nm), polydispersity indexes (PDI), zeta potentials (mV) and number average diameters (nm) are collected in the following table.

TABLE

DLS and SEM characterisation of nanoparticles obtained by co-nanoprecipitation of p($HPMA_{50}$-$EGDMA_{0.9}$), $PEO_{45}$-p($HPMA_{120}$) and p($HPMA_{50}$-$EGDMA_{0.9}$)$_x$:$PEO_{45}$-p($HPMA_{120}$)$_y$ (x:y) acetone solutions into water.

| Entry | Sample | Ratio (%) | DLS Z-average Diameter (d · nm) | PDI | DLS Number Diameter Average (d · nm) | SEM Number Diameter Average (d · nm) | Zeta Potential (mV) |
|---|---|---|---|---|---|---|---|
| 1 | p($HPMA_{50}$-EGDMA) | 100 | 148 | 0.08 | 112 ± 6 | 117 | −40.5 |
| 2 | $PEO_{45}$-p($HPMA_{120}$) | 100 | 296 | 0.135 | 188 ± 80 | 190 | −17.5 |
| 3 | p($HPMA_{50}$-EGDMA):$PEO_{45}$-p($HPMA_{120}$) | 90:10 | 107 | 0.075 | 84 ± 2 | 81 | −19.3 |
| 4 | p($HPMA_{50}$-EGDMA):$PEO_{45}$-p($HPMA_{120}$) | 80:20 | 126 | 0.046 | 99 ± 4 | 105 | −24.4 |
| 5 | p($HPMA_{50}$-EGDMA):$PEO_{45}$-p($HPMA_{120}$) | 70:30 | 116 | 0.067 | 93 ± 3 | 117 | −20.6 |
| 6 | p($HPMA_{50}$-EGDMA):$PEO_{45}$-p($HPMA_{120}$) | 60:40 | 119 | 0.107 | 91 ± 1 | 88 | −21.5 |
| 7 | p($HPMA_{50}$-EGDMA):$PEO_{45}$-p($HPMA_{120}$) | 50:50 | 174 | 0.093 | 137 ± 3 | 110 | −19.7 |

The branched statistical copolymerisation of HPMA and EGDMA was initiated with ethyl 2-bromo isobutyrate (EBIB) using the catalytic system previously described in the following ratio [Macroinitiator]:[EGDMA]:[Monomer]:[Cu(I)Cl]:[Bpy]=1:0.9:50:1:2. The molar ratio of [EGDMA]/[EBIB]<1 is a crucial parameter in order to have control over the branching reaction and avoid gelation. As expected, the presence of EGDMA dramatically increases the polymer molecular weight (for example, $M_w$=295,000 Da) and dispersity (Đ=7.56) in contrast to the linear amphiphilic polymer which displayed a monomodal narrow molecular weight distribution. In addition, $^1$H NMR analysis of both linear $PEO_{45}$-p($HPMA_{120}$) and branched p($HPMA_{50}$-$EGDMA_{0.9}$) showed high monomer conversion (>98%).

Nanoprecipitation and Co-Nanoprecipitation

Polymeric nanoparticles were prepared by nanoprecipitation which corresponds to a solvent switch through a rapid precipitation into water (ambient temperature). It is hypothesised that during the association of the p($HPMA_{50}$-$EGDMA_{0.9}$) hydrophobic branched core, the linear HPMA chains from the diblock copolymer also become incorporated into the hydrophobic core allowing the $PEO_{45}$ (2 kDa) chains to be present at the surface of the resulting particles and prevent aggregation by steric stabilisation. Varying weight fractions of p($HPMA_{50}$-$EGDMA_{0.9}$)$_x$:$PEO_{45}$-p($HPMA_{102}$)$_y$ (x:y) were dissolved in acetone at a total concentration of 5 mg mL$^{-1}$ for six hours to ensure complete solubilisation. Rapid precipitation of 1 mL of the polymer solution into 5 mL of water gave a final nanoparticle concentration of 1 mg mL$^{-1}$ after complete acetone evaporation.

Self assembly of the branched p($HPMA_{50}$-$EGDMA_{0.9}$) and amphiphilic $PEO_{45}$-p($HPMA_{120}$) polymers during co-nanoprecipitation from acetone into $H_2O$ produced well defined particles indicated by the low PDI values (0.046-0.107) and size homogeneity respectively obtained from DLS measurements and SEM observations.

The co-nanoprecipitated particles exhibited zeta potential values ranging between −19 mV and −25 mV (Table 1, entries 3-7).

Salt Stability

The salt stability of the co-precipitated particles was demonstrated by adding aliquots (20 µL) of an aqueous 0.5M NaCl salt solution to 1 mL of the nanoprecipitated dispersions. Z-average diameters and PDI were measured during a period of 0-21 days.

Co-nanoprecipitated particles demonstrated excellent salt stability over 21 days after 20 µL addition, and maintainance of narrow polydispersity. Nanoparticles containing only branched vinyl polymer crashed out of solution immediately on NaCl addition whereas nanoparticles containing both branched vinyl polymer and diblock amphiphiic copolymer remained as a stable nanoparticle dispersion. SEM analysis of the nanoparticles (0.1 mg mL$^{-1}$) showed the spherical nature of the particles and co-nanoprecipitates made up of groups of particles.

Figure 5:
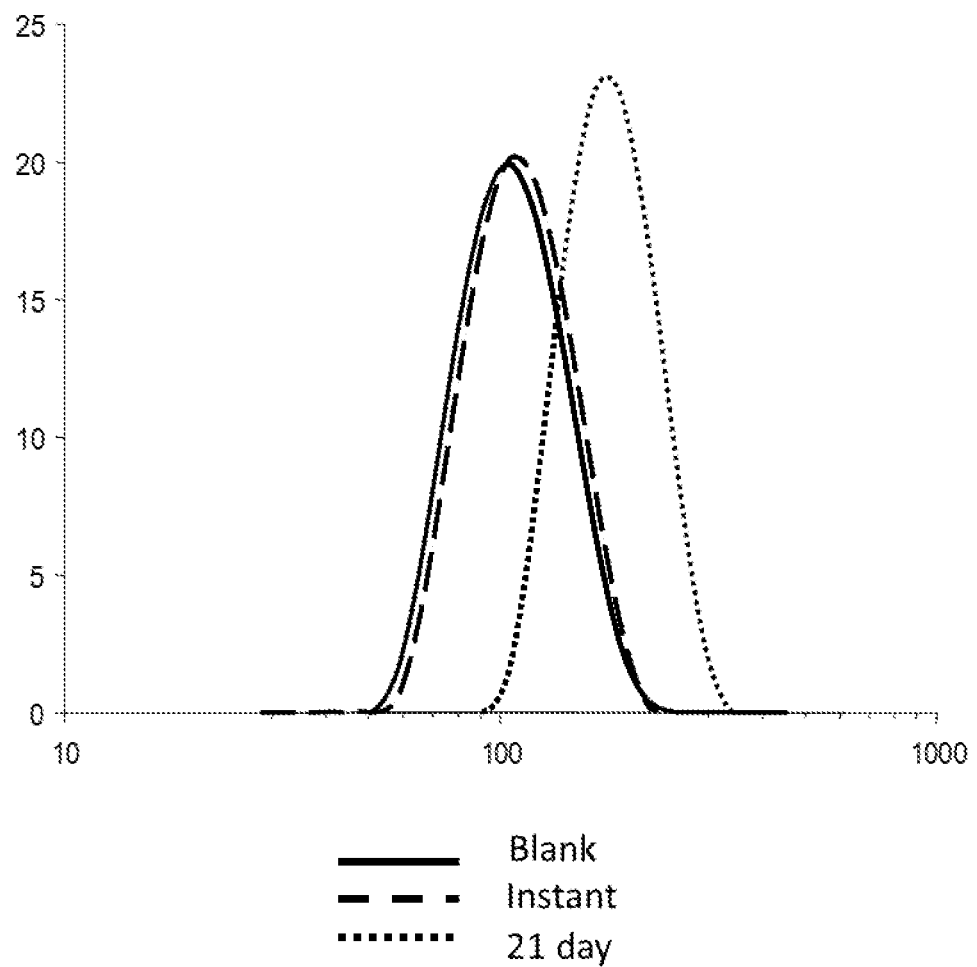

FIG. 5 shows how the z-average diameter and PDI vary on addition of NaCl (20 µL 0.5M NaCl) to a 1 mg mL$^{-1}$ aqueous dispersion of p($HPMA_{50}$-$EGDMA_{0.9}$):$PEO_{45}$-p($HPMA_{120}$) 60:40. The vertical axis denotes intensity (percent) and the horizontal axis shows z-average diameter (d, nm). Solid line: before addition. Dashed line: immediately after NaCl addition. Dotted line: 21 days after NaCl addition.

Figure 6:
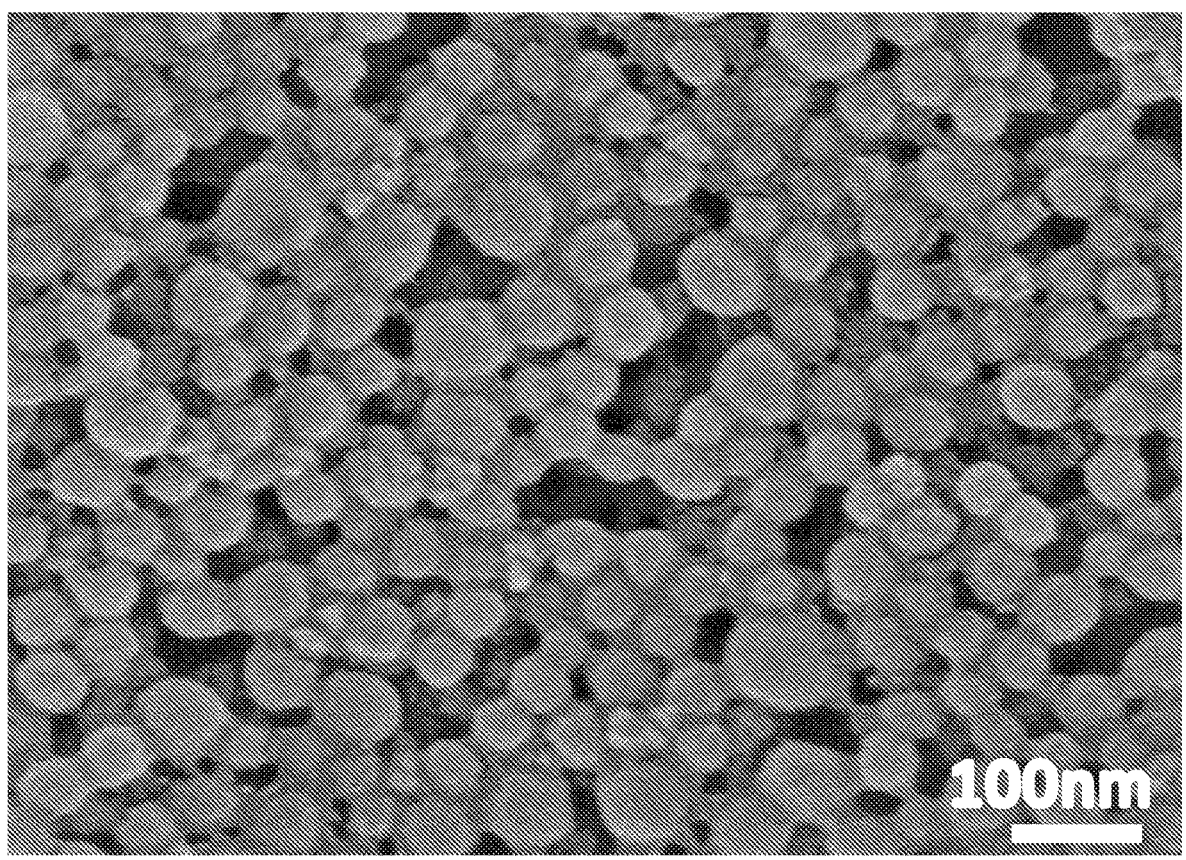
FIG. 6 shows an SEM image of nanoparticles in accordance with the present invention.
Figure 7:
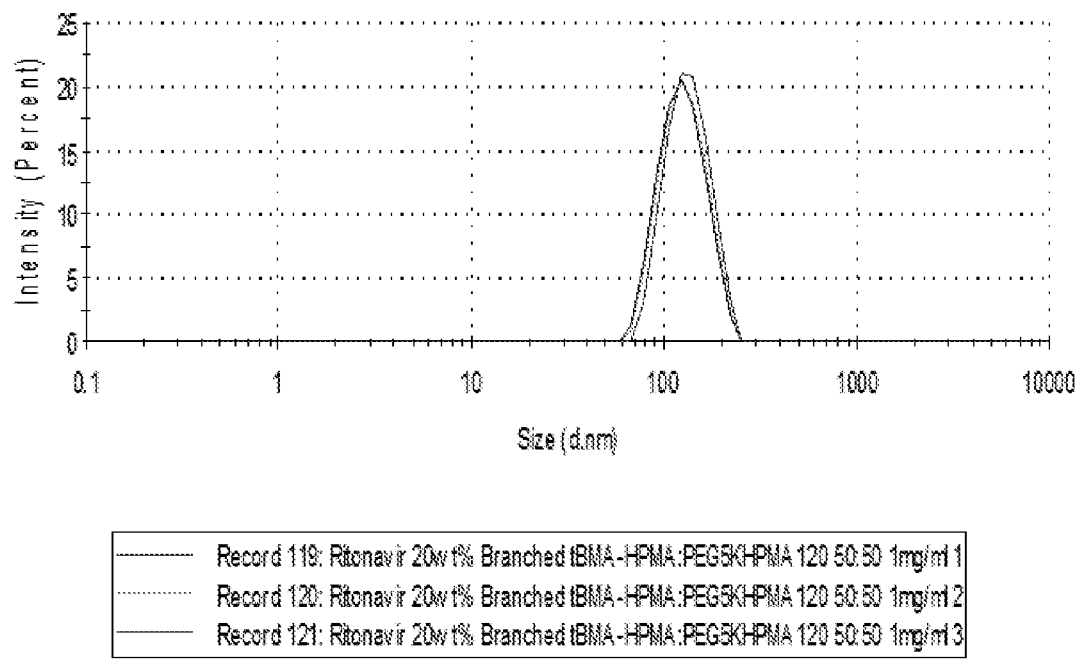
FIGS. 7 to 12 show particle size distributions of drug-loaded particles.
Figure 8:
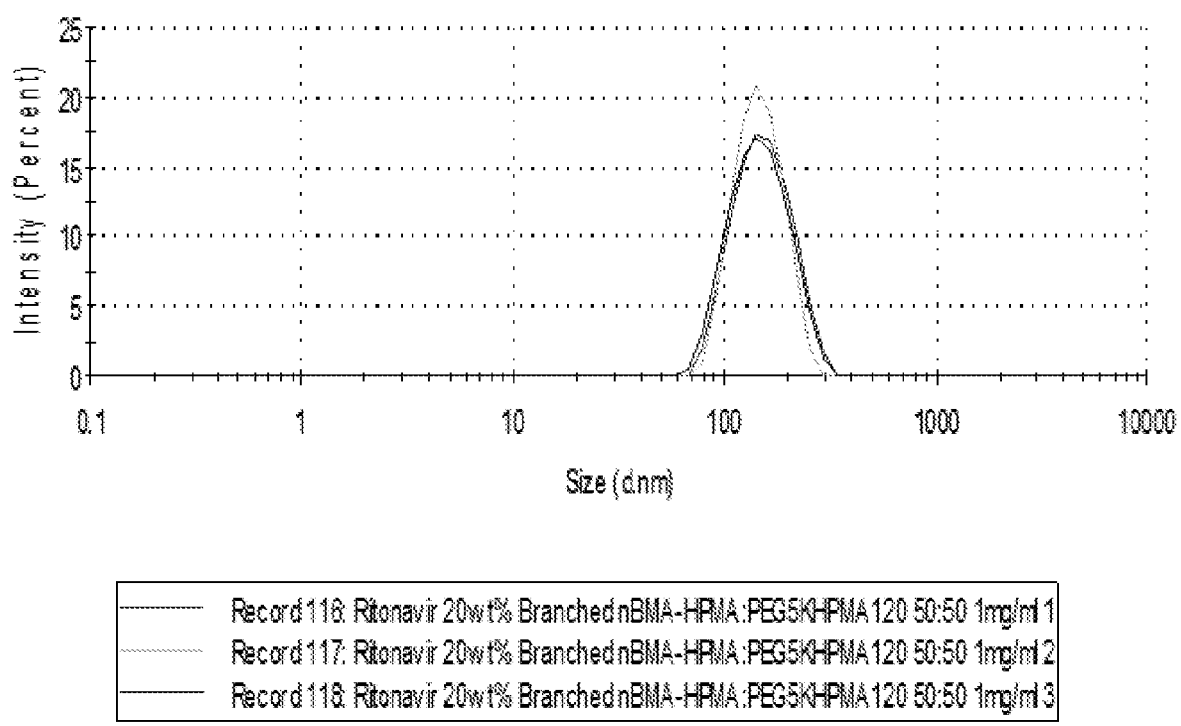
Figure 9:
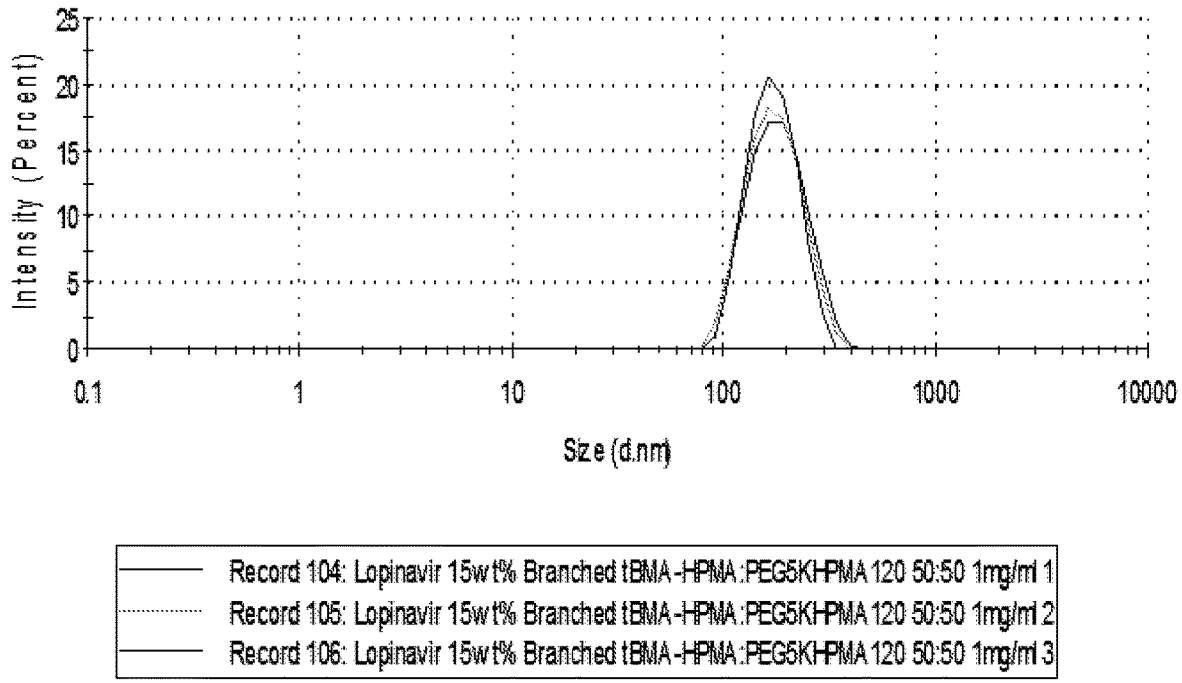
Figure 10:
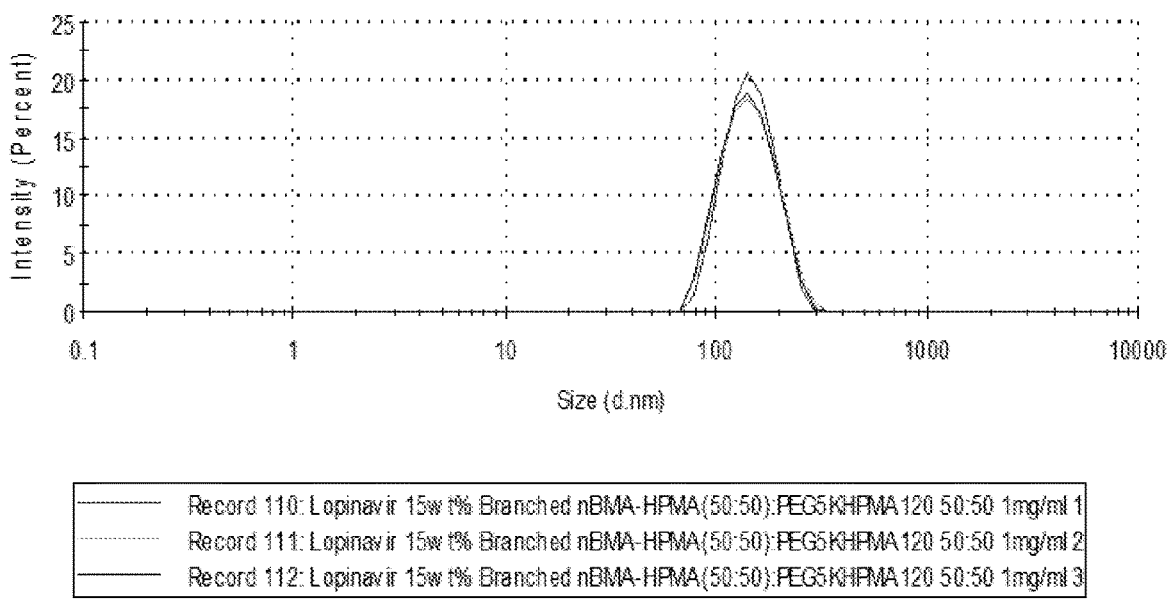
Figure 11:
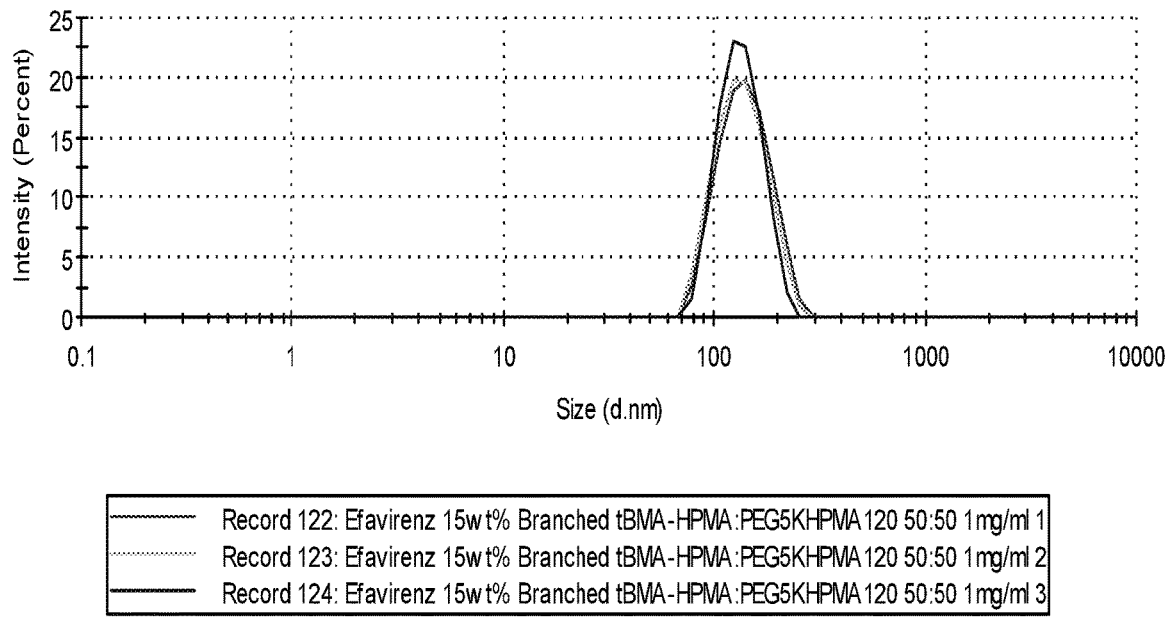
Figure 12:
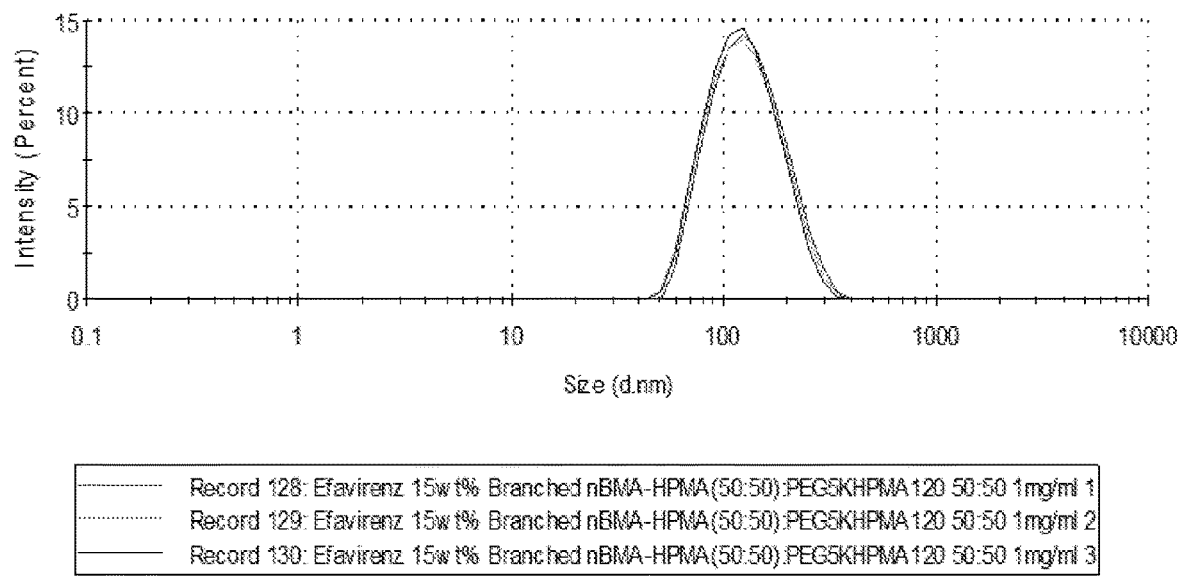

FIG. 6 shows a scanning electron microscopy image of p(HPMA$_{50}$-EGDMA$_{0.9}$):PEO$_{45}$-p(HPMA$_{120}$) 60:40; 1 mg mL$^{-1}$.

Conclusions from Example 1

Example 1 shows that the addition of an amphiphilic diblock 'stabiliser' (PEO 2000 Da) to a branched hydrophobic polymer at low concentrations followed by co-nanoprecipitation can form particles with desirable z-average diameters and very narrow PDI values. A range of co-nanoprecipitated particles can be prepared. The co-nanoprecipitated particles offer enhanced stability due to the introduction of a steric stabiliser. This relies upon the formation of an outer layer of material that prevents particles coming into close proximity.

Loading of HIV Antivirals

The use of the nanoparticles to load various drugs including the following HIV antiretrovirals was investigated:

Efavirenz:

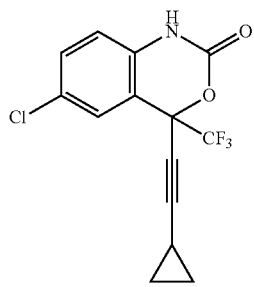

Lopinavir:

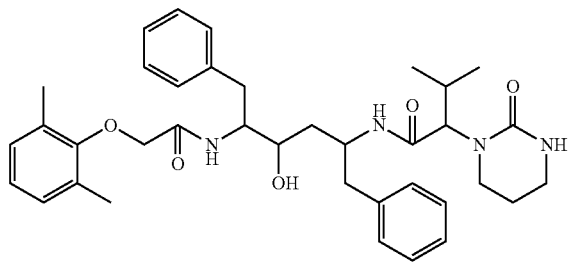

Ritonavir:

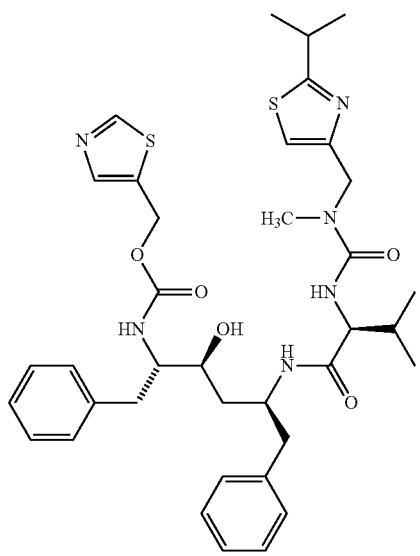

Drugs could be encapsulated inside the polymer particles in a reliable and reproducible manner, allowing particles to be produced with very narrow particle size distributions.

The use of branched vinyl polymers with a blend of two monomers [HPMA plus either tert-butyl methacrylate (tBMA) or n-butyl methacrylate (nBMA)] in the hydrophobic core was found to be particularly effective in allowing high drug loadings to be achieved. Good results were also obtained when nBMA was used as the only monofunctional monomer in the branched vinyl polymer.

The results are shown in FIGS. 7 to 12 as follows:

| FIG. | Drug and loading | Branched polymer (EGDMA used as brancher in each case) | Z-ave | PdI |
|---|---|---|---|---|
| 7 | Ritonavir 20 wt % | tBMA-HPMA | 123 nm | 0.062 |
| 8 | Ritonavir 20 wt % | nBMA-HPMA | 141 nm | 0.072 |
| 9 | Lopinavir 15 wt % | tBMA-HPMA | 166 nm | 0.060 |
| 10 | Lopinavir 15 wt % | nBMA-HPMA | 137 nm | 0.063 |
| 11 | Efavirenz 15 wt % | tBMA-HPMA | 131 nm | 0.037 |
| 12 | Efavirenz 15 wt % | nBMA-HPMA | 117 nm | 0.131 |

The block copolymer utilised to form particles shown in FIGS. 7-12 was PEG 5K-HPMA$_{120}$ and the ratio of branched polymer to linear polymer was 50:50.

The drug loading could be increased by further tailoring the polymer chemistry to allow drug loadings of 25 wt % to be achieved for Efavirenz. The drug-loaded particles were stable extended periods of time. Further experiments investigated the loading of different drug types and details of these (and also of polymer synthesis and co-nanoprecipitation in this context) are as follows.

Typical Nanoparticle Preparation Including 10 Wt % Loading for Efavirenz, Ritonavir and Lopinavir During a typical nanoparticle preparation, 5.5 mL of a 1 mg/mL acetone solution of efavirenz, ritonavir or lopinavir is added to a vial and left to evaporate overnight. To this vial 25 mg of the branched polymer and 25 mg of the polymer diblock were added and dissolved in 10 mL of acetone during 6-8 hours to ensure complete solubilisation. 1 mL of the 5 mg/mL solution of polymers and dissolved drug was added to 5 mL of stirring distilled water (500 rpm) and left for 24 hours for complete acetone evaporation (final concentration of polymer 1 mg/mL).

Anti-Cancer Drugs

Other examples of drugs which can be incorporated are anti-cancer drugs.

Irinotecan is a hydrophobic anticancer drug and SN-38 is a hydrophobic anticancer active metabolite of irinotecan.

Irinotecan in particular was effectively encapsulated at 10 wt % or 15 wt % into co-nanoprecipitated particles with low PdI values, for example where the branched polymer comprised nBMA or tBMA-HPMA and the amphiphilic polymer comprised PEG5K-HPMA120.

Irinotecan (Typical 10 wt % Loading)

During a typical nanoparticle preparation 5.5 mL of a 1 mg/mL acetone solution of irinotecan was added to a vial and left to evaporate overnight. To this vial, 25 mg of the branched polymer and 25 mg of the polymer diblock were added and dissolved in 10 mL of acetone during 6-8 hours to ensure complete solubilisation. 1 mL of the 5 mg/mL solution of polymers and dissolved drug was added to 5 mL of stirring water (500 rpm) and left for 24 hours for complete acetone evaporation.

SN-38 (Typical 2 wt % Loading)

During a typical nanoparticle preparation 1.03 mL of a 1 mg/mL THF/Acetonitrile (50:50) solution of SN-38 was added to a vial and left to evaporate overnight. To this vial 25 mg of the branched polymer core and 25 mg of polymer diblock were added and dissolved in 10 mL of acetone during 6-8 hours to ensure complete solubilisation. 1 mL of the 5 mg/mL solution of polymers and dissolved drug was added to 5 mL of stirring water (500 rpm) and left for 24 hours for complete acetone evaporation.

Preparation of SN-38 Nanoparticles by DMSO Dialysis

During a typical nanoparticle preparation by dialysis, 2.65 mL of a 1 mg/mL DMSO solution of SN-38, 25 mg of the branched polymer core and 25 mg of the polymer diblock were added and dissolved in 7.35 mL of DMSO during 6-8 hours to ensure complete solubilisation. 1 mL of the 5 mg/mL solution of polymers was added to a dialysis bag with a molecular weight cut off (MWCO) of 2000 g/mol and left to dialyse in distilled water over 4 days (changing the water every 4 hours)

ATRP Polymerisation—Formation of the Branched Polymer Core p(HPMA$_{50}$-EGDMA$_{0.9}$)

The targeted number average degree of polymerisation (DP$_n$) was 50 repeat units. During a typical ATRP synthesis, EBIB initiator (0.14 g, 0.69 mmol 1 eq.) and HPMA (5 g, 34.68 mmol 50 eq.) were added to a round-bottomed flask equipped with a nitrogen inlet/outlet and a stirrer bar. Methanol was added (50 wt/wt %, based on HPMA) and the solution was stirred vigorously under nitrogen for 10-15 minutes. The branching agent EGDMA (0.12 g, 0.62 mmol 0.9 eq. to EBIB initiator), copper catalyst Cu(I)Cl (0.069 g, 0.69 mmol 1 eq.) and bpy (0.22 g, 1.39 mmol 2 eq.) were added to the flask and the temperature was fixed at 30° C. The reaction was monitored by $^1$H NMR spectroscopy and terminated with methanol when the HPMA monomer had reached >99% conversion. The polymer was purified using Dowex Marathon exchange beads (~12 g) to remove excess copper catalyst followed by passing the sample through a basic alumina column. Excess THF was removed under vacuum to concentrate the sample before precipitation into cold hexane. The resulting polymer was confirmed by $^1$H NMR in MeOD, triple detection GPC with an eluent of THF.

The polymerisation was carried out for all other monomers:

nBMA p(nBMA$_{50}$-EGDMA$_{0.9}$), tBMA p(tBMA$_{50}$-EGDMA$_{0.9}$), HPMA-nBMA p(HPMA$_{25}$-nBMA$_{25}$-EGDMA$_{0.9}$) and HPMA-tBMA p(HPMA$_{25}$-tBMA$_{25}$-EGDMA$_{0.9}$)

Example Synthesis of Poly(Ethylene Glycol) Mono-Functional ATRP Macro-Initiator (PEO$_x$-Br) (when x=45, the Macroinitiator is Referred to Herein as PEG 2K)

During a typical synthesis, PEO$_{45}$-OH (30 g, 15 mmol, 1 eq.) was dissolved in 100 mL of toluene in the presence of triethylamine (2.275 g, 22.5 mmol, 1.5 eq.) and 4-dimethylaminopyridine (0.092 g, 0.75 mmol 0.05 eq.) in a two necked round-bottomed flask fitted with an addition funnel, a nitrogen inlet/outlet and a stirrer bar. 2-bromo-2-methylpropionyl bromide (5.175 g, 22.5 mmol, 1.5 eq.) diluted with 25 mL of toluene was placed in the addition funnel. The reactor was put under stirring, cooled at about 0° C. in an ice bath and the 2-bromo-2-methylpropionyl bromide solution was added slowly over a period of 20-30 min. After the addition was completed, the reactor was allowed to reach room temperature and was left to stir for 24 hours. The formation of a white precipitate (triethylamine salt) indicated the progress of the reaction. Then, the reaction medium was warmed up in a water bath at about 50° C., filtered and concentrated on the rotary evaporator. The resulting product was diluted in acetone and purified by precipitation in petroleum ether. The last step was repeated once and the product was finally dried under vacuum at 40° C. for 24 hours. The resulting macro-initiator was recovered with 70% yield and its structure was confirmed by $^1$H NMR in D$_2$O, triple detection GPC with an eluent of DMF and MALDI-TOF mass spectrometry.

PEG 5K

Same synthesis for PEO-5K initiator—PEO$_{114}$-OH was used rather than PEO$_{45}$-OH.

ATRP Polymerisation—Synthesis of Linear PEO$_{45}$-p (HPMA$_{120}$)

The targeted number average degree of polymerisation (DP$_n$) was 120 repeat units. In a typical ATRP synthesis, PEO$_{45}$-Br macroinitiator (0.62 g, 0.29 mmol 1 eq.) and HPMA (5 g, 34.68 mmol 120 eq.) were added to a round-bottomed flask equipped with a nitrogen inlet/outlet and a stirrer bar. Methanol was added (33.5 w/v %, based on HPMA) and the solution was stirred vigorously under nitrogen for 10-15 minutes. The copper catalyst Cu(I)Cl (0.029 g, 0.29 mmol 1 eq.) and bpy (0.09 g, 0.58 mmol 2 eq.) were added to the flask and the temperature was fixed at 30° C. The reaction was monitored by $^1$H NMR spectroscopy and terminated with methanol when the HPMA monomer had reached 99% conversion. The polymer was purified using Dowex Marathon exchange beads (~12 g) to remove excess copper catalyst followed by passing the sample through a basic alumina column. Excess THF was removed under vacuum to concentrate the sample before precipitation into petroleum ether 30/40. The resulting polymer was confirmed by $^1$H NMR in d$_6$-DMSO, triple detection GPC with an eluent of DMF.

The procedure described above was used for all other number average degree of polymerisations for HPMA and the ATRP of PEO5K-nBMA120.

Other Drugs and Other Drug Incorporation Methods

The present invention is also compatible with numerous other drugs and also with other methods of incorporating drugs including not just encapsulation as described previously but also chemical bonding, sometimes referred to as conjugation, either to the branched polymer or the linear polymer or both components of the particle.

In this context Ibuprofen was used as a model drug. Free ibuprofen was encapsulated, and it was also bonded via its acid functionality to produce a prodrug model.

Ibuprofen Work—Prodrug Model

Synthesis of the Ibuprofen (IBU) Modified HPMA (IbuPMA)

During a typical synthesis HPMA (1.5 g, 10.40 mmol 1 eq.), Ibuprofen (2.79 g, 13.53 mmol 1.3 eq), DMAP (0.64 g, 5.5 mmol, 0.5 eq) and DCC (2.79 g, 13.53 mmol, 1.3 eq) were dissolved in 40 mL of THF in a round bottom flask and stirred at ambient temperature for 24 hours. The DCU salt was filtered and washed with THF followed by rotary evaporation. DCM (100 mL) was added and washed with 1M sodium bisulfate solution to remove excess DCU, then dried over MgSO4, concentrated in vacuo and stored at 0° C.

ATRP Polymerisation—Incorporated IBU Monomer: Targeted Total DP80 Composition PEO$_{114}$-(HPMA$_{60}$-IbuPMA$_{20}$)

The targeted number average degree of polymerisation (DP$_n$) was HPMA$_{60}$-IbuPMA$_{20}$. PEO$_{114}$-Br macroinitiator (0.59 g, 0.12 mmol 1 eq.) and HPMA (1 g, 6.94 mmol 60 eq.) and IbuPMA (0.77 g 2.3 mmol, 20 eq.) were added to a round-bottomed flask equipped with a nitrogen inlet/outlet and a stirrer bar. Methanol was added (37 w/w %, based on HPMA+IbuPMA) and the solution was stirred vigorously under nitrogen for 10-15 minutes. The copper catalyst Cu(I)Cl (0.0114 g, 0.12 mmol 1 eq.) and bpy (0.036 g, 0.23 mmol 2 eq.) were added to the flask and the temperature was fixed at 30° C. The reaction was monitored by $^1$H NMR spectroscopy and terminated with methanol when the monomers had reached 99% conversion. The polymer was purified using a neutral alumina column flushed with THF to remove excess copper catalyst. Excess THF was removed under vacuum to concentrate the sample before precipitation into cold petroleum ether 30/40. The resulting polymer was confirmed by $^1$H NMR in MeOD, triple detection GPC with an eluent of THF.

Post Modification of $PEO_{114}$-$HPMA_{120}$-Targeted 40 HPMA Monomer Units $PEO_{114}$-$HPMA_{120}$ (1 g, 0.033 mmol, 1 eq.), Ibuprofen (0.27 g, 1.33 mmol, 40 eq.), DCC (0.274 g, 1.33 mmol, 40 eq.) and DMAP ($1\times10^{-3}$ g) were dissolved in THF (12 mL) and left over 24 hours. The DCU was filtered off and washed with THF and concentrated in vacuo. The excess DMAP and DCU was dissolved in DCM and washed with 1M sodium bisulfate and dried with $MgSO_4$ and dried under vacuum.

ATRP Polymerisation—Branched IBU Modified Copolymer p($HPMA_{60}$-$IBU_{20}$-$EGDMA_{0.9}$)

The targeted degree of polymerisation ($DP_n$) was 50 repeat units. During a typical ATRP synthesis, EBIB initiator (0.024 g, 0.12 mmol 1 eq.) and HPMA (1.04 g, 7.23 mmol 60 eq.) and IbuPMA (0.8 g, 2.41 mmol, 20 eq.) were added to a round-bottomed flask equipped with a nitrogen inlet/outlet and a stirrer bar. Methanol was added (50 wt/wt %, based on HPMA) and the solution was stirred vigorously under nitrogen for 10-15 minutes. The branching agent EGDMA (0.021 g, 0.11 mmol 0.9 eq. to EBIB initiator), copper catalyst Cu(I)Cl (0.012 g, 0.12 mmol 1 eq.) and bpy (0.038 g, 0.24 mmol 2 eq.) were added to the flask and the temperature was fixed at 30° C. The reaction was monitored by $^1$H NMR spectroscopy and terminated with methanol when the HPMA monomer had reached >99% conversion. The polymer was purified using a neutral alumina column flushed with THF. Excess THF was removed under vacuum to concentrate the sample before precipitation. The polymer was precipitated from MeOH into cold petroleum ether 30/40. The resulting polymer was confirmed by $^1$H NMR in MeOD, triple detection GPC with an eluent of THF.

Nanoparticle Preparation

IBU Modified Diblock—p$(EO)_{114}$-p($HPMA_{60}$-HPMA:$IBU_{20}$):p($HPMA_{50}$-$EGDMA_{0.9}$)

During a typical nanoparticle preparation, 25 mg of $PEO_{114}$-p($HPMA_{60}$-HPMA:$IBU_{20}$) and 25 mg of p($HPMA_{50}$-$EGDMA_{0.9}$) were added to 10 mL of MeOH during 6-8 hours to ensure complete solubilisation over 6-8 hours. 1 mL of the 5 mg/mL solution of polymers was added to 5 mL of stirring distilled water (500 rpm) and left for 24 hours for complete evaporation.

IBU Modified Branched Polymer Core p($HPMA_{60}$-$IBU_{20}$-$EGDMA_{0.9}$)

During a typical nanoparticle preparation, 25 mg of $PEO_{114}$-p($HPMA_{120}$) and 25 mg of p($HPMA_{60}$-$IbuPMA_{20}$-$EGDMA_{0.9}$) were added to 10 mL of MeOH during 6-8 hours to ensure complete solubilisation over 6-8 hours. 1 mL of the 5 mg/mL solution of polymers was added to 5 mL of stirring distilled water (500 rpm) and left for 24 hours for complete evaporation.

The same procedure can be repeated for other variations of the nanoparticles using the experimental above. For free IBU addition, this can simply be added into the methanol before solubilisation at the desired ratio to allow mixtures of encapsulated IBU and IBU-prodrugs within the particles.

Further Example Showing that a Different Type of Block Copolymer—a Tri-Block A-B-A (Hydrophobic-Hydrophilic-Hydrophobic) Polymer—can be Prepared, and Used in Combination with a Branched Polymer and Drug Encapsulation To illustrate a variation of the chemistry which may be used within the scope of the present invention, a bifunctional initiator was prepared and used as the "B" block in the preparation of an "A-B-A" tri-block copolymer. This tri-block copolymer was then used in combination with a branched vinyl polymer and drug molecules to form suitable co-nanoprecipitated particles.

Synthesis of PEG Bifunctional Macroinitiator

During a typical synthesis, OH-$PEG_{104}$-OH ($M_n$~4600 g, 1 equiv. 20 g, 4.3 mmol), TEA (3 equiv. 0.013 mol, 1.83 mL) and DMAP (0.1 equiv, 4.0 mmol, 0.053 g) were added to toluene (80 mL) in a two necked round bottom flask fitted with a nitrogen inlet/outlet and stirrer bar. α-Bromo isobutyryl bromide (3 equiv. 13 mmol, 1.61 mL) was diluted in toluene (20 mL) and added drop-wise over 15 minutes via a dropping funnel and left stirring over 24 hours. The reaction mixture was then filtered and the excess solvent removed in vacuo. The product was dissolved in a minimal amount of acetone, and precipitated into cold petroleum ether 40-60° C. (1:10 product:solvent) and left to dry under vacuum at 40° C. for 48 hours.

Synthesis of p($HPMA_x$-b-$PEG_{104}$-b-$HPMA_x$) Block Polymer

During a typical synthesis, Br-$PEG_{104}$-Br (1 equiv. 2.17 g, 0.43 mmol), HPMA (80 equiv. 5.0 g, 34.6 mmol), anisole (0.1 ml) and anhydrous methanol (50 wt %) were added to a round bottomed flask fitted with an nitrogen inlet/outlet and stirrer bar. To this solution, anhydrous methanol (50 wt %, based on HPMA), CuCl (1 equiv. 0.042 g, 0.43 mmol) and bpy (2 equiv. 0.135 g, 0.867 mmol) were added and the reaction mixture was degassed under nitrogen for 15-20 minutes. The reaction was left stirring for 24 hrs and high conversion was confirmed $^1$H NMR spectra. The reaction was terminated by addition of methanol (~50 ml) and the remaining solution was then passed through a neutral alumina column to remove the catalytic system. The product was purified by concentrating the solution in vacuo and precipitation of the polymer into cold hexane (1:10 product:solvent). The resulting block copolymer was analysed by $^1$H NMR and GPC.

Branched p($DEAEMA_{50}$) polymer was synthesized as previously described.

Encapsulation of Drug Molecules into Co-Nanoprecipitated Particles Consisting of an A-B-A Triblock and a Branched Polymer Core A stock solution of solubilised drug molecules (Ritonavir and Lopinavir) was added to a sample vial (up to 5 wt % of each) and the acetone was left to evaporate. To this vial, the branched polymer, A-B-A triblock polymer (varying ratios of each) and acetone were added to make up a solution of 5 mg/mL. To ensure complete solubilisation this solution was left rolling over 24 hours. During a typical co-nanoprecipitation, 1 mL of the polymer/drug solution was rapidly added to 5 mL of stirring water. The solution was left stirring overnight to ensure complete solvent removal and subsequent nanoparticles dispersions were measured by dynamic light scattering.

Stable nanoparticles resulted, whether encapsulating Ritonavir alone, Lopinavir alone, or a 1:1 by weight mixture of both.

Particles Containing Branched Polymers and Linear Dendritic Hybrids

A second group of particles in accordance with the present invention are those which contain branched polymers and linear dendritic hybrids.

Examples of Polymers Prepared by ATRP and of Combinations of Such Polymers in Particles Some non-limiting examples of components used in branched vinyl polymers and block copolymers have been described and defined above.

Linear dendritic hybrids may comprise monomers as referred to above, and additionally, of course, comprise dendrons. In that context, some non-limiting examples of components used in polymers of the present invention include the following.

G2-M: a generation 2 dendron initiator having the structure:

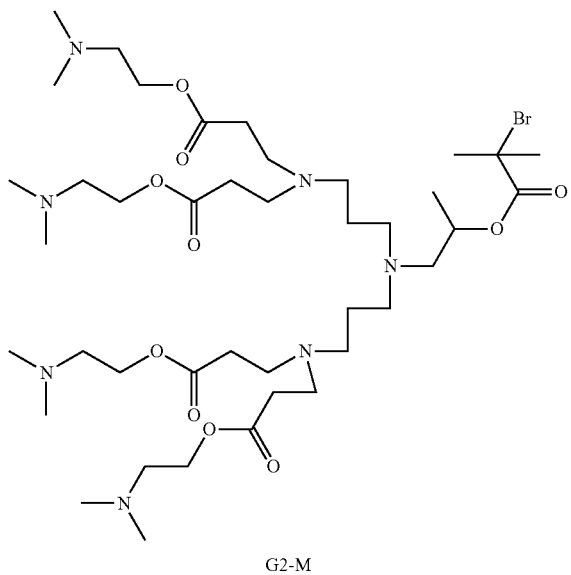 [SMILES: CC(CN(CCCN(CCC(=O)OCCN(C)C)CCC(=O)OCCN(C)C)CCCN(CCC(=O)OCCN(C)C)CCC(=O)OCCN(C)C)OC(=O)C(C)(C)Br]

G2-M

G2-Bz: a generation 2 dendron initiator with benzyl-functionalised ends having the structure:

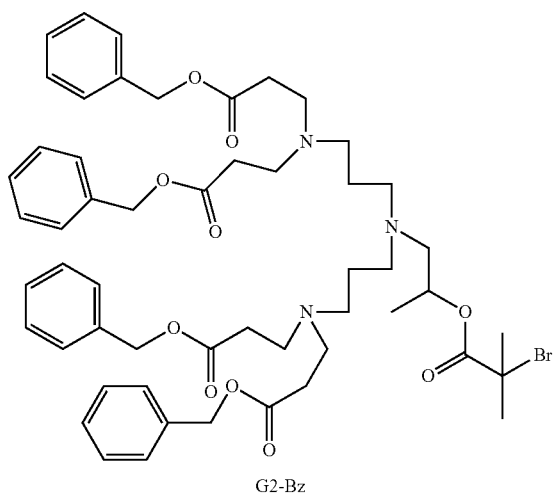 [SMILES: CC(CN(CCCN(CCC(=O)OCc1ccccc1)CCC(=O)OCc1ccccc1)CCCN(CCC(=O)OCc1ccccc1)CCC(=O)OCc1ccccc1)OC(=O)C(C)(C)Br]

G2-Bz

G1-M: a generation 1 dendron initiator having the structure:

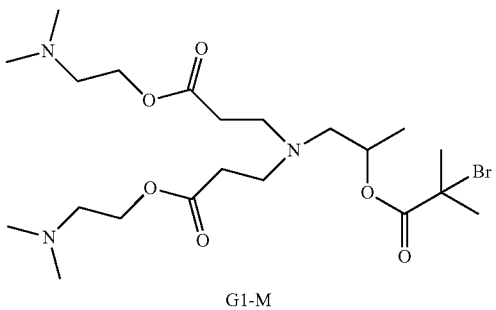 [SMILES: CC(CN(CCC(=O)OCCN(C)C)CCC(=O)OCCN(C)C)OC(=O)C(C)(C)Br]

G1-M

G0-M: a generation 0 initiator having the structure:

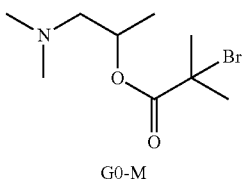

G0-M

Figure 13:
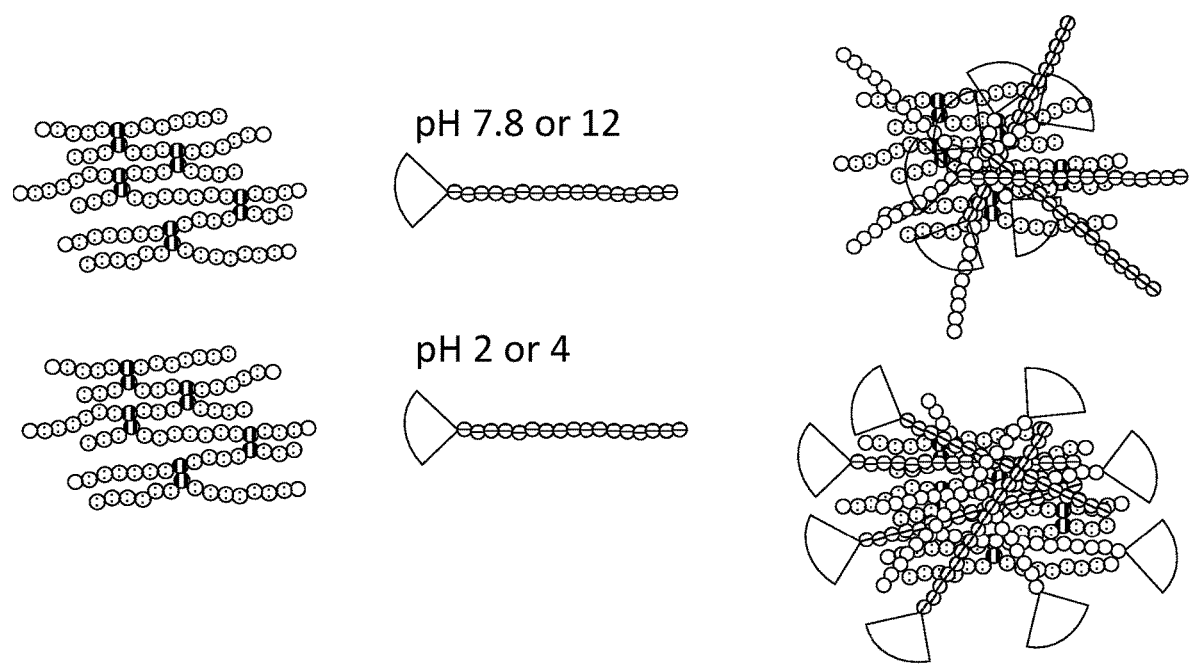
FIG. 13 shows a schematic representation of a branched polymer, linear dendritic hybrid, and a nanoparticle of the present invention containing both, in two different architectures.
Figure 16:
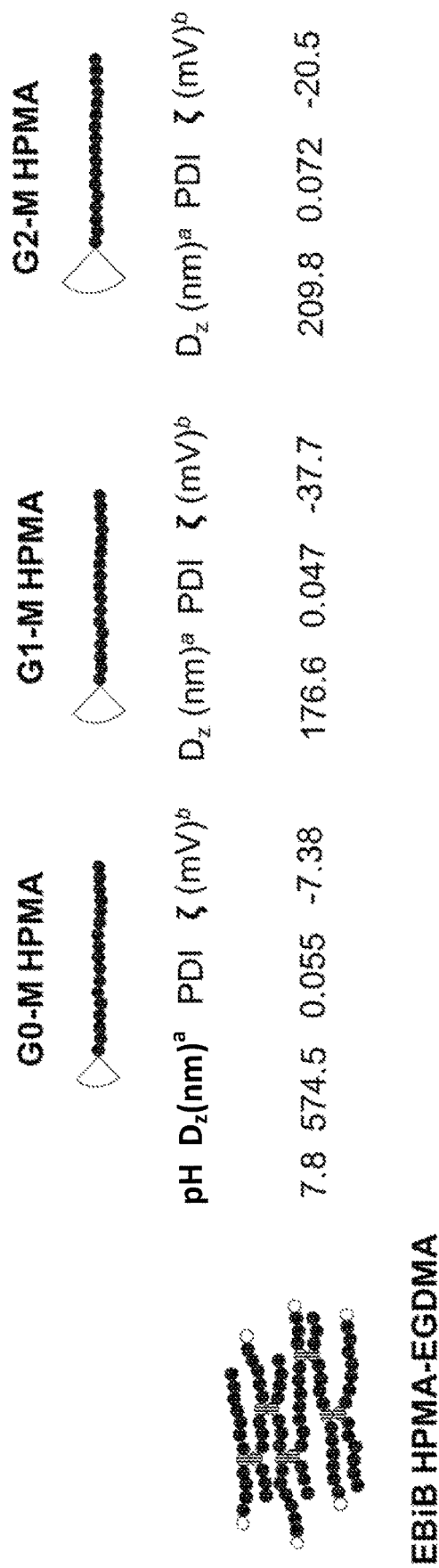
Figure 17:
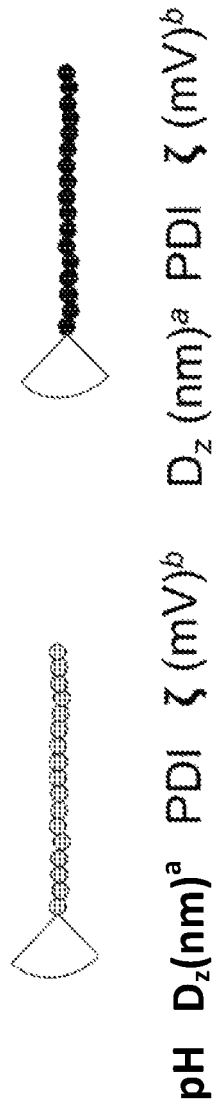

Schematic representations of co-nanoprecipitates of branched polymers and linear dendritic hybrids are shown in FIG. 13. The dendrons are shown as wedges. In some examples (top right) the dendrons are hypothesised to be at least partially within the particles whereas in other examples (bottom right) the dendrons are hypothesised to be mainly exposed at the surface. This can be controlled by varying pH, for example when using pH responsive materials such as DEAEMA.

Figure 19:
FIG. 19 shows an SEM image of some nanoparticles.

Some examples of combinations of polymers, and the properties of the resultant particles under different pH conditions, are shown in FIGS. 14 to 18. FIGS. 14 to 18 use the abbreviation CNP which denotes co-nanoprecipitates. An SEM image is shown in FIG. 19 for the pH 7.8 particles containing EBIB tBuMA-EGDMA and G2-M DEAEMA (FIG. 14).

[a] All diameters are given as z-average values as measured by dynamic light scattering.

[b] All zeta potentials are given as surface charge values as measured by dynamic light scattering Further Examples of Combinations of Branched Vinyl Polymers and Linear Dendritic Hybrids Further examples of combinations of branched vinyl polymers and linear dendritic hybrids, prepared by ATRP, include those listed in the following table. This exemplifies a range of chemistries (including hydrophilic, hydrophobic, and pH responsive) and different copolymer approaches (including block copolymers and statistical copolymers). It will also be seen that the block copolymer approach may be combined with the linear dendritic hybrid approach, i.e. a linear dendritic hybrid may comprise a dendron connected to one block which is then connected to another block. Furthermore, in place of G2-M or G2-Bz, G1-M, G0-M or EBIB may be used instead, i.e. the linear chains may be initiated by smaller dendrons or by initiators which are not dendrons (in which case the materials co-precipitated with the branched vinyl polymer are not linear dendritic hybrids but merely linear polymers, of which the present invention is concerned with a subset, namely block copolymers).

| branched polymer | linear dendritic hybrid |
|---|---|
| EBIB-HPMA$_{50}$-EGDMA$_{0.95}$ | G2-M-HPMA$_{50}$ |
| as above | G2-M-DEAEMA$_{50}$ |
| EBIB-tBuMA$_{50}$-EGDMA$_{0.95}$ | G2-M-DEAEMA$_{50}$ |
| as above | G2-M-HPMA$_{50}$ |
| as above | G2-M-PtBuMA$_{50}$ |
| as above | Block copolymers: G2-M-PDEAEMA$_{25}$-tBuMA$_{25}$ or G2-M-PDEAEMA$_{17}$-tBuMA$_{33}$ or G2-M-PDEAEMA$_{33}$-tBuMA$_{17}$ |
| as above | as above, except that the copolymers are random copolymers rather than block copolymers |
| as above | G2-Bz-DEAEMA$_{50}$ |
| EBIB-DEAEMA$_{50}$-EGDMA$_{0.95}$ | G2-M-DEAEMA$_{50}$ and |
| EBIB-DEAEMA$_{50}$-BDME$_{2.0}$ | as above |
| EBIB-DEAEMA$_{50}$-EGDMA$_{0.95}$ | G2-M-HPMA$_{50}$ |
| EBIB-HPMA$_x$-DEAEMA$_y$-EGDMA$_{0.9}$ (copolymer wherein x, y = 25, 25 or 17, 33 or 33, 17) | G2-M-HPMA$_{50}$ |
| as above | G2-M-DEAEMA$_{50}$ |
| as above | G2-M-HPMA$_x$-DEAEMA$_y$ (random copolymer wherein x, y = 17, 33 or 25, 25 or 33, 17) |
| as above | (as above, except that the copolymer is a diblock copolymer rather than a random copolymer) |
| EBIB-HPMA$_{50}$-EGDMA$_{0.95}$ | G2-M-HPMA$_x$-DEAEMA$_y$ (random copolymer wherein x, y = 17, 33 or 25, 25 or 33, 17) |
| as above | (as above, except that the copolymer is a diblock copolymer rather than a random copolymer) |
| EBIB-DEAEMA$_{50}$-EGDMA$_{0.95}$ | G2-M-HPMA$_x$-DEAEMA$_y$ (random copolymer wherein x, y = 17, 33 or 25, 25 or 33, 17) |
| as above | (as above, except that the copolymer is a diblock copolymer rather than a random copolymer) |

The materials in the above table may for example be co-nanoprecipitated in a ratio of 90:10 branched:linear. One suitable method involves: dropping 0.2 ml (5 mg ml$^{-1}$ in acetone, THF or IPA) of linear polymer and 1.8 ml (5 mg ml$^{-1}$ in acetone, THF or IPA) of branched polymer into 10 ml water; and allowing the organic solvent to evaporate overnight to form a 1 mg ml$^{-1}$ nanoparticle dispersion in water.

A range of pH conditions may be used and optionally conditions and monomers may be chosen to provide particular structures. Merely by way of non-limiting example, at low pH protonation of amine moieties (e.g. in DEAEMA or in dendrons) means that amine moieties are more likely to be exposed towards the outside of the particles Examples of Polymers Prepared by Ring Opening Polymerization and of Such Polymers in Particles Another method of polymerization which can be used in the present invention is ring opening polymerisation (ROP). For example, lactone monomers may be ring opened by reaction with alcohols under suitable conditions as known in the art.

For example, the polymerization of caprolactone monomer may be initiated by benzyl alcohol to produce benzyl—polycaprolactone (abbreviated herein as Bz-PCL).

The ring opening of single lactone rings such as polycaprolactone results in linear polymers.

Branched polymers may be obtained by using branchers, e.g. monomers which have two lactone rings connected together, e.g. BOD (4,4'-bioxepanyl-7,7'-dione). The following scheme shows a method of preparing BOD:

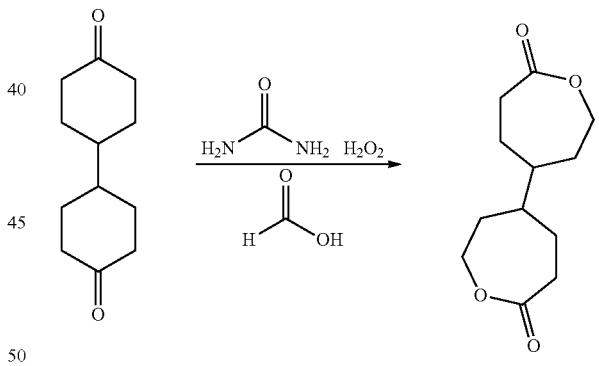

A branched polyester may be prepared by copolymerizing a monofunctional lactone (e.g. caprolactone) and a difunctional lactone (e.g. BOD) using an initiator (e.g. Bz-OH):

Such branched polycaprolactones may be used instead of the branched vinyl polymers, in combination with linear polymers (i.e. block copolymers or linear dendritic hybrids).

Examples of combinations of branched polycaprolactone (prepared by ROP) and linear dendritic hybrids (prepared by ATRP), which we have co-nanoprecipitated, include those listed in the following table. As before, in place of G2 it is possible to instead use G1, G0 or EBIB.

| branched polycaprolactone | linear dendritic hybrid |
|---|---|
| Bz-PCL$_{50}$-BOD$_{0.6}$ | G2-M-DEAEMA$_{50}$ |
| as above | G2-M-HPMA$_{50}$ |

-continued

| branched polycaprolactone | linear dendritic hybrid |
|---|---|
| as above | block copolymers: G2-M-DEAEMA$_{25}$-tBuMA$_{25}$ or G2-M-DEAEMA$_{17}$-tBuMA$_{33}$ or G2-M-DEAEMA$_{33}$-tBuMA$_{17}$ |
| as above | as above except random copolymers instead of block copolymers |

ROP may also be used to prepare the linear dendritic hybrid (or other linear polymer component), and ROP and ATRP may be combined.

Polyesters may also be used in the linear dendritic hybrid, and non-limiting examples of suitable initiators for ROP in that context include the following.

G2-pOH: a generation 2 dendron bearing a hydroxyl group to initiate ROP, of the following structure:

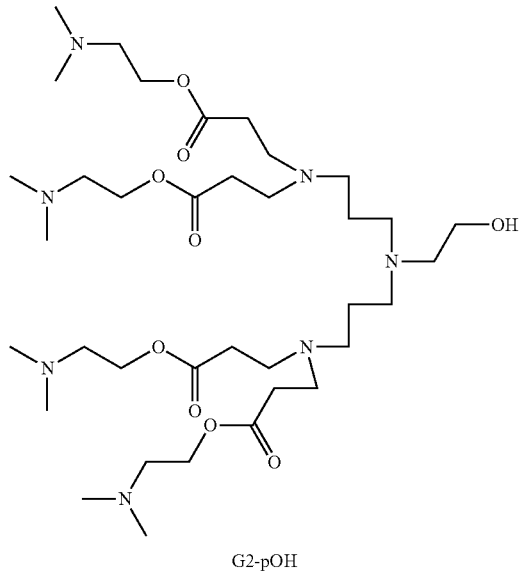 [SMILES: CN(C)CCOC(=O)CCN(CCCN(CCO)CCCN(CCC(=O)OCCN(C)C)CCC(=O)OCCN(C)C)CCC(=O)OCCN(C)C]

G2-pOH

G1-pOH: a generation 1 dendron bearing a hydroxyl group to initiate ROP, of the following structure:

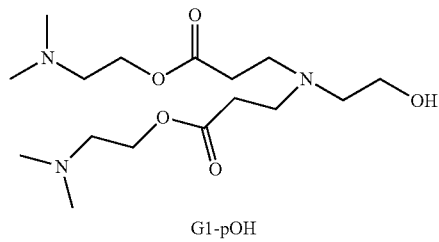 [SMILES: CN(C)CCOC(=O)CCN(CCO)CCC(=O)OCCN(C)C]

G1-pOH

G0-pOH: a generation 0 initiator of the following structure:

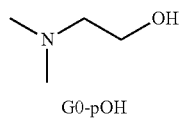

G0-pOH

Examples of linear dendritic hybrids which may be combined with branched polymers, e.g. Bz-PCL$_{50}$-BOD$_{0.6}$, include:
G1-p-PCL$_{50}$-DEAEMA$_{20}$
G2-p-PCL$_{50}$
G2-p-PCL$_{30}$
G2-p-PCL$_{20}$ Example Experimental Procedures for ATRP and ROP Polymerisations and for the Preparation of Materials Used in these Polymerisations 1. Polymerisation by ATRP
1.1 ATRP Dendron Initiator Synthesis
1.1.1 Synthesis of G1-M-OH 2-(Dimethylamino)ethyl acrylate (6.0 g, 42 mmol, 6 eq.) was added to a 50 mL round 2 necked round-bottomed flask containing isopropanol (IPA) (12 mL). The flask was deoxygenated under a positive N$_2$ purge for 10 minutes. 1-amino-2-propanol (0.5246 g, 7.0 mmol, 1 eq.) dissolved in IPA (12 mL) was added drop wise while the solution was stirring in an ice bath under a positive flow of N$_2$. The final mixture was stirred for a further 10 minutes at 0° C. before being allowed to warm to room temperature and left stirring for 48 hrs. The solvent was removed and the product left to dry in vacuo overnight. Found C, 57.45; H, 9.77; N, 11.12%. C$_{17}$H$_{35}$N$_3$O$_5$ requires, C, 56.43; H, 9.68; N, 11.62%. $^1$H NMR (400 MHz, CDCl$_3$) δ 1.08 (d, 3H), 2.18-2.62 (m, 22H), 2.69 (m, 2H), 2.89 (m, 2H), 3.77 (m, 1H), 4.16 (m, 4H). $^{13}$C NMR (100 MHz, CDCl3) δ 19.8, 32.6, 45.6, 49.7, 57.8, 62.0, 63.7, 76.9, 128.4, 130.9, 172.5. m/z (ES MS) 362.3 [M+H]+, 384.3 [M+Na]+.

1.1.2 Synthesis of G2-M-OH 2-(Dimethylamino)ethyl acrylate (6.0 g, 42 mmol, 6 eq.) was added to a 50 mL round 2 necked round-bottomed flask containing IPA (12 mL). The flask was deoxygenated under a positive N$_2$ purge for 10 minutes. Bis(3-aminopropyl)amino)propan-2-ol (1.3221 g, 6.984 mmol, 1 eq.) dissolved in IPA (12 mL) was added drop wise while the solution was stirring in an ice bath under a positive flow of N$_2$. The final mixture was stirred for a further 10 minutes at 0° C., allowed to warm to room temperature and left stirring for 48 hrs. The solvent was removed and the product left to dry in vacuo overnight. Found C, 58.32; H, 9.92; N, 12.87%. C$_{37}$H$_{75}$N$_7$O$_9$ requires, C, 58.27; H, 9.84; N, 12.86%. $^1$H NMR (400 MHz, CDCl$_3$) δ 1.13 (d, 3H), 1.67 (m, 4H), 2.26-2.65 (m, 50H), 2.77 (m, 8H), 3.87 (m, 1H), 4.17 (m, 8H). m/z (ES MS) 762.6 [M+H]+, 784.6 [M+Na]+.

1.1.3 Synthesis of G0-M 1-dimethylamino-2-propanol (1.1207 g, 10.86 mmol, 1 eq.), triethanolamine (TEA) (1.5390 g, 15.2 mmol, 1.4 eq.) and dimethyl amino pyridine (DMAP) (132.7 mg, 1.086 mmol, 0.1 eq.) were added to a 250 mL 2 necked round-bottomed flask containing dichloromethane (DCM) (160 mL). The flask was deoxygenated under a positive N$_2$ purge for 10 minutes. α-bromoisobutyryl bromide (2.622 g, 1.4 mL, 11.4 mmol, 1.05 eq.) was added drop wise while the solution was stirring in an ice bath under a positive flow of N$_2$. The reaction mixture was allowed to warm to room temperature and left stirring overnight. The organic phase was washed with saturated sodium hydrogen carbonate (NaHCO$_3$) solution (3×30 mL). The solution was dried with anhydrous Na$_2$SO$_4$. Found C, 42.87; H, 7.20; N, 5.55%. C$_9$H$_{18}$NO$_2$Br requires, C, 42.86; H, 7.14; N, 5.55%. $^1$H NMR (400 MHz, CDCl$_3$) δ 1.27 (d, 3H), 1.89 (s, 6H), 2.17-2.55 (m, 8H), 5.07 (m, 1H). $^{13}$C NMR (100 MHz, CDCl3) δ 17.6, 30.9, 46.1, 56.1, 63.5, 70.6, 76.9, 170.8. m/z (ES MS) 252 [M+H]+.

1.1.4 Synthesis of G1-M

G1-OH (1.1207 g, 10.86 mmol, 1 eq.), TEA (1.5390 g, 15.2 mmol, 1.4 eq.) and DMAP (132.7 mg, 1.086 mmol, 0.1 eq.) were added to a 250 mL 2 necked round-bottomed flask containing DCM (160 mL). The flask was deoxygenated under a positive $N_2$ purge for 10 minutes. α-bromoisobutyryl bromide (2.622 g, 1.4 mL, 11.4 mmol, 1.05 eq.) was added drop wise while the solution was stirring in an ice bath under a positive flow of $N_2$. The reaction mixture was allowed to warm to room temperature and left stirring overnight. The organic phase was washed with saturated sodium hydrogen carbonate ($NaHCO_3$) solution (3×160 mL). The solution was dried with anhydrous $Na_2SO_4$ and the product left to dry in vacuo overnight. Found C, 49.41; H, 7.90; N, 8.23%. $C_{21}H_{40}N_3O_6Br$ requires, C, 49.41; H, 7.84; N, 8.24%. $^1$H NMR (400 MHz, CDCl$_3$) δ 1.22 (d, 3H), 1.89 (s, 6H), 2.24-2.69 (m, 22H), 2.83 (m, 4H), 4.20 (m, 4H), 5.0 (m, 1H). $^{13}$C NMR (100 MHz, CDCl3) δ 18.6, 30.9, 32.8, 50.0, 56.4, 58.8, 60.3, 69.6, 77.2, 125.7, 144.3, 172.3. m/z (ES MS) 510.2 [M+H]+, 534.2 [M+Na]+.

1.1.5 Synthesis of G2-M

G2-OH (5.1431 g, 6.749 mmol, 1 eq.), TEA (0.9561 g, 9.449 mmol, 1.4 eq.) and DMAP (82.5 mg, 0.6749 mmol, 0.1 eq.) were added to a 250 mL 2 necked round-bottomed flask containing DCM (160 mL). The flask was deoxygenated under a positive $N_2$ purge for 10 minutes. α-bromoisobutyryl bromide (1.629 g, 0.88 mL, 7.087 mmol, 1.05 eq.) was added drop wise while the solution was stirring in an ice bath under a positive flow of $N_2$. The reaction mixture was allowed to warm to room temperature and left stirring overnight. The organic phase was washed with saturated sodium hydrogen carbonate ($NaHCO_3$) solution (3×160 mL). The solution was dried with anhydrous $Na_2SO_4$ and the product left to dry in vacuo overnight. Found C, 54.05; H, 8.85; N, 10.76%. $C_{41}H_{80}N_7O_{10}Br$ requires, C, 54.01; H, 8.78; N, 10.76%. $^1$H NMR (400 MHz, CDCl$_3$) δ 1.26 (d, 3H), 1.56 (m, 4H), 1.91 (s, 6H), 2.22-2.67 (m, 50H), 2.76 (m, 8H), 4.19 (m, 8H), 5.04 (m, 1H). $^{13}$C NMR (100 MHz, CDCl3) δ 24.5, 25.5, 28.4, 45.6, 62.2, 64.2, 77.2, 173.5. m/z (ES MS) 912.5 [M+H]+, 934.5 [M+Na]+, 950.5 [M+K]+.

1.1.6 Synthesis of G2-Bz-OH

Benzyl acrylate (6.7966 g, 42 mmol, 6 eq.) was added to a 50 mL round 2 necked round-bottomed flask containing IPA (12 mL). The flask was deoxygenated under a positive $N_2$ purge for 10 minutes. Bis(3-aminopropyl)amino)propan-2-ol (1.3221 g, 6.984 mmol, 1 eq.) dissolved in IPA (12 mL) was added drop wise while the solution was stirring in an ice bath under a positive flow of $N_2$. The final mixture was stirred for a further 10 minutes at 0° C., allowed to warm to room temperature and left stirring for 48 hrs. The solvent was removed and the product left to dry in vacuo overnight.

1.1.7 Synthesis of G2-Bz

G2-Bz (1.664 g, 1.86 mmol, 1 eq.), TEA (0.2639 g, 2.6 mmol, 1.4 eq.) and DMAP (22.8 mg, 0.1866 mmol, 0.1 eq.) were added to a 250 mL 2 necked round-bottomed flask containing DCM (110 mL). The flask was deoxygenated under a positive $N_2$ purge for 10 minutes. α-bromoisobutyryl bromide (0.5354 g, 0.29 mL, 2.329 mmol, 1.25 eq.) was added drop wise while the solution was stirring in an ice bath under a positive flow of $N_2$. The reaction mixture was allowed to warm to room temperature and left stirring overnight. The organic phase was washed with saturated sodium hydrogen carbonate ($NaHCO_3$) solution (3×110 mL). The solution was dried with anhydrous $Na_2SO_4$ and the product left to dry in vacuo overnight. Found C, 63.40; H, 6.96; N, 4.18%. $C_{53}H_{68}N_3O_{10}Br$ requires, C, 64.44; H, 6.89; N, 4.26%. $^1$H NMR (400 MHz, CDCl$_3$) δ 1.22 (d, 3H), 1.54 (m, 4H), 1.90 (s, 6H), 2.24-2.65 (m, 18H), 2.77 (m, 8H), 5.00 (m, 1H), 5.09 (s, 8H), 7.33 (m, 20H). $^{13}$C NMR (100 MHz, CDCl3) δ 18.1, 30.6, 32.3, 44.1, 48.8, 51.7, 52.7, 66.7, 76.7, 128.6, 135.8, 144.1, 172.3. m/z (ES MS) 988.4 [M+H]+.

1.2 pH Responsive Brancher Synthesis

1.2.1 Synthesis of 1,4-Butanediol Di(Methacryoyloxy)-Ethyl Ether (BDME)

1,4-butanediol divinyl ether (BDVE) (5.6 ml, 35.21 mmol) was added to a two-necked 250 ml round bottomed flask equipped with a condenser, a magnetic stirrer and a positive flow of nitrogen. A small amount of radical inhibitor 4-tert-butylcatechol (end of a spatula) was added and the mixture deoxygenated using a nitrogen purge for 15 minutes. Once dissolved, the temperature was raised to 70° C. Methacrylic acid (MAA) (14.9 ml, 175.8 mmol) was added dropwise over 10 minutes through a septa. The reaction was allowed to proceed at 70° C. for a further 6 hours with stirring. After this time, the reaction was stopped by cooling and exposing to the air. The crude product was dissolved in chloroform (100 ml) and washed with basic $H_2O$ (~pH12, 3×100 ml). The combined washings were collected and dried over $NaSO_4$ and the solvent removed by rotary evaporation.

(Found: C, 61.45; H, 8.28%. $C_{16}H_{26}O_6$ requires C, 61.15; H, 8.28%); $^1$H NMR (400 MHz; CDCl$_3$; Me$_4$Si) δ 1.44 (6H, d, $CH_3CH$), 1.65 (4H, m, $CH_2CH_2CH_2$), 1.95 (6H, s, $CH_3C=CH2$), 3.50-3.69 (4H, m, $OCH_2CH_2$), 5.60 and 6.15 (4H, 2s, $CH_2=CCH_3$) and 5.95-5.99 (2H, q, $CHCH_3$). $^{13}$C NMR (400 MHz; CDCl$_3$; Me$_4$Si) δ 18.27 (s), 20.83 (s), 26.29 (s) 68.85 (s), 96.93 (s), 125.90 (s), 136.37 (s) and 167.01 (s). m/z (EI) 314.2 ($M^+$-$C_{16}H_{26}O_6$ requires 314).

1.3 Polymerisation of HPMA

1.3.1 Polymerisation of $HPMA_{50}$

In a typical synthesis, targeting a number average degree of polymerisation ($DP_n$)=50 monomer units P(HPMA)$_{50}$; $n_{HPMA}/n_{Initiator}$: 50), bpy (173.3 mg, 1.1096 mmol, 2 eq.), HPMA (4 g, 27.7 mmol, 50 eq.) and methanol (MeOH) (56% v/v based on HPMA) were placed into a 25 mL round-bottomed flask. The solution was stirred and deoxygenated using a nitrogen ($N_2$) purge for 15 minutes. Cu(I)Cl (54.9 mg, 0.5548 mmol, 1 eq.) was added to the flask and left to purge for a further 5 minutes. G2-M (0.5054 g, 0.5548 mmol, 1 eq.) was added to the flask under a positive flow of $N_2$, and the solution was left to polymerise at 30° C. Reactions were terminated when >99% conversion was reached, as judged by $^1$H NMR (cf. FIG. 8), by exposure to oxygen and addition of THF. The catalyst residues were removed by passing the mixture over a basic alumina column. THF was removed under vacuum to concentrate the sample before precipitation into hexane and drying in the vacuum oven overnight.

1.3.2 Polymerisation of $HPMA_{50}$-$EGDMA_x$

In a typical synthesis, targeting a number average degree of polymerisation ($DP_n$)=50 monomer units P(HPMA)$_{50}$; $n_{HPMA}/n_{Initiator}$: 50), bpy (173.3 mg, 1.1096 mmol, 2 eq.), HPMA (4 g, 27.7 mmol, 50 eq.), EGDMA (99.0 mg, 0.4993 mmol, 0.9 eq) and methanol (MeOH) (38.9% v/v based on HPMA) were placed into a 25 mL round-bottomed flask. The solution was stirred and deoxygenated using a nitrogen ($N_2$) purge for 15 minutes. Cu(I)Cl (54.9 mg, 0.5548 mmol, 1 eq.) was added to the flask and left to purge for a further 5 minutes. EBIB (0.1082 g, 0.5548 mmol, 1 eq.) was added to the flask under a positive flow of $N_2$, and the solution was left to polymerise at 30° C. Reactions were terminated when >99% conversion was reached, as judged by $^1$H NMR, by exposure to oxygen and addition of THF. The catalyst residues were removed by passing the mixture over a basic alumina column. THF was removed under vacuum to concentrate the sample before precipitation into hexane.

1.4 Polymerisation of DEAEMA 1.4.1 Polymerisation of DEAEMA$_{50}$

In a typical synthesis, targeting a DP$_n$=50 monomer units PDEAEMA$_{50}$; n$_{DEAEMA}$/n$_{Initiator}$: 50), bpy (134.9 mg, 0.8637 mmol, 2 eq.), DEAEMA (4 g, 21.59 mmol, 50 eq.) and IPA (56% v/v based on DEAEMA) were placed into a 25 mL round-bottomed flask. The solution was stirred and deoxygenated using a nitrogen (N$_2$) purge for 15 minutes. Cu(I)Cl (42.8 mg, 0.4318 mmol, 1 eq.) was added to the flask and left to purge for a further 5 minutes. G2-M (0.3934 g, 0.4318 mmol, 1 eq.) was added to the flask under a positive flow of N$_2$, and the solution was left to polymerise at 40° C. Reactions were terminated when >99% conversion was reached, as judged by $^1$H NMR, by exposure to oxygen and addition of acetone. The catalyst residues were removed by passing the mixture over a basic alumina column. Acetone was removed under vacuum to concentrate the sample before precipitation into cold petroleum ether (40° C.-60° C.) and drying in the vacuum oven overnight.

1.4.2 Polymerisation of DEAEMA$_{50}$-EGDMA$_x$

In a typical synthesis, targeting a DP$_n$)=50 monomer units PDEAEMA$_{50}$; n$_{DEAEMA}$/n$_{Initiator}$: 50), bpy (134.9 mg, 0.8637 mmol, 2 eq.), DEAEMA (4 g, 21.59 mmol, 50 eq.), EGDMA (77.0 mg, 0.3886 mmol, 0.9 eq) and IPA (38.9% v/v based on DEAEMA) were placed into a 25 mL round-bottomed flask. The solution was stirred and deoxygenated using a N$_2$ purge for 15 minutes. Cu(I)Cl (42.8 mg, 0.4318 mmol, 1 eq.) was added to the flask and left to purge for a further 5 minutes. EBIB (84.2 mg, 0.4318 mmol, 1 eq.) was added to the flask under a positive flow of N$_2$, and the solution was left to polymerise at 40° C. Reactions were terminated when >99% conversion was reached, as judged by $^1$H NMR, by exposure to oxygen and addition of acetone. The catalyst residues were removed by passing the mixture over a basic alumina column. Acetone was removed under vacuum to concentrate the sample before precipitation into cold petroleum ether (40° C.-60° C.) and drying in the vacuum oven overnight. The polymerisation conditions and procedure is identical to those described for linear polymers above.

1.4.3 Polymerisation of DEAEMA$_{50}$-BDME

In a typical synthesis, targeting a DP$_n$)=50 monomer units PDEAEMA$_{50}$; n$_{DEAEMA}$/n$_{Initiator}$: 50), bpy (134.9 mg, 0.8637 mmol, 2 eq.), DEAEMA (4 g, 21.59 mmol, 50 eq.), BDME (291.2 mg, 0.8637 mmol, 0.9 eq) and IPA (38.9% v/v based on DEAEMA) were placed into a 25 mL round-bottomed flask. The solution was stirred and deoxygenated using a N$_2$ purge for 15 minutes. Cu($_I$)Cl (42.8 mg, 0.4318 mmol, 1 eq.) was added to the flask and left to purge for a further 5 minutes. EBIB (84.2 mg, 0.4318 mmol, 1 eq.) was added to the flask under a positive flow of N$_2$, and the solution was left to polymerise at 40° C. Reactions were terminated when >99% conversion was reached, as judged by $^1$H NMR, by exposure to oxygen and addition of acetone. The catalyst residues were removed by passing the mixture over a basic alumina column. Acetone was removed under vacuum to concentrate the sample before precipitation into cold petroleum ether (40° C.-60° C.) and drying in the vacuum oven overnight. The polymerisation conditions and procedure is identical to those described for linear polymers above.

1.5 Polymerisation of tBuMA 1.5.1 Polymerisation of tBuMA$_{50}$

In a typical synthesis, targeting a number average degree of polymerisation (DP$_n$)=50 monomer units (tBuMA$_{50}$); n$_{tBuMA}$/n$_{Initiator}$: 50), bpy (175.7 mg, 1.125 mmol, 2 eq.), tBuMA (4 g, 28.129 mmol, 50 eq.) and aqueous isopropanol (IPA/H$_2$O) (92.5/7.5%) (50.4% v/v based on tBuMA) were placed into a 50 mL round-bottomed flask. The solution was stirred and deoxygenated using a nitrogen (N$_2$) purge for 15 minutes. Cu(I)Cl (55.7 mg, 0.5626 mmol, 1 eq.) was added to the flask and left to purge for a further 5 minutes. G2-M (0.3934 g, 0.5626 mmol, 1 eq.) was added to the flask under a positive flow of N$_2$, and the solution was left to polymerise at 20° C. and samples were taken periodically from the reaction mixture for $^1$H NMR analysis. Reactions were terminated when >99% conversion was reached, as judged by $^1$H NMR, by exposure to oxygen and addition of THF. The catalyst residues were removed by passing the mixture over a basic alumina column. THF was removed under vacuum to concentrate the sample before precipitation into hexane and drying in the vacuum oven overnight.

1.5.2 Polymerisation of tBuMA$_{50}$-EGDMA$_{95}$

In a typical synthesis, targeting a number average degree of polymerisation (DP$_n$)=50 monomer units (tBuMA$_{50}$); n$_{tBuMA}$/n$_{Initiator}$: 50), bpy (175.7 mg, 1.125 mmol, 2 eq.), tBuMA (4 g, 28.13 mmol, 50 eq.), EGDMA (105.9 mg, 0.5345 mmol) and aqueous isopropanol (IPA/H$_2$O) (92.5/7.5%) (38.4% v/v based on tBuMA) were placed into a 50 mL round-bottomed flask. The solution was stirred and deoxygenated using a nitrogen (N$_2$) purge for 15 minutes. Cu(I)Cl (55.7 mg, 0.5626 mmol, 1 eq.) was added to the flask and left to purge for a further 5 minutes. EBIB (0.1097 g, 0.5626 mmol, 1 eq.) was added to the flask under a positive flow of N$_2$, and the solution was left to polymerise at 20° C. and samples were taken periodically from the reaction mixture for $^1$H NMR analysis. Reactions were terminated when >99% conversion was reached, as judged by $^1$H NMR, by exposure to oxygen and addition of THF. The catalyst residues were removed by passing the mixture over a basic alumina column. THF was removed under vacuum to concentrate the sample before precipitation into hexane and drying in the vacuum oven overnight.

1.6 Polymerisation of DEAEMA-tBuMA 1.6.1 Polymerisation of G2-DEAEMA$_x$-stat-tBuMA$_y$ In a typical synthesis, targeting a DP$_n$=50 monomer units PDEAEMA$_{25}$-tBuMA$_{25}$; n$_{DEAEMA}$/n$_{Initiator}$: 50), bpy (134.9 mg, 0.8637 mmol, 2 eq.), DEAEMA (2 g, 10.80 mmol, 25 eq.), tBuMA (1.5352, 10.80 mmol, 25 eq.) and IPA/H$_2$O (92.5/7.5%) (30.6% v/v based on DEAEMA/tBuMA) were placed into a 50 mL round-bottomed flask. The solution was stirred and deoxygenated using a nitrogen (N$_2$) purge for 15 minutes. Cu(I)Cl (42.8 mg, 0.4318 mmol, 1 eq.) was added to the flask and left to purge for a further 5 minutes. G2-M (0.3934 g, 0.4318 mmol, 1 eq.) was added to the flask under a positive flow of N$_2$, and the solution was left to polymerise at 40° C. Reactions were terminated when >99% conversion was reached, as judged by $^1$H NMR, by exposure to oxygen and addition of acetone. The catalyst residues were removed by passing the mixture over a basic alumina column. Acetone was removed under vacuum to concentrate the sample before precipitation into cold petroleum ether (40° C.-60° C.) and drying in the vacuum oven overnight.

1.6.2 Polymerisation of EBIB-DEAEMA$_x$-stat-tBuMA$_y$-EGDMA$_{0.9}$

In a typical synthesis, targeting a DP$_n$=50 monomer units PDEAEMA$_{25}$-tBuMA$_{25}$; n$_{DEAEMA}$/n$_{Initiator}$: 50), bpy (134.9 mg, 0.8637 mmol, 2 eq.), DEAEMA (2 g, 10.80 mmol, 25 eq.), tBuMA (1.5352, 10.80 mmol, 25 eq.), EGDMA (77 mg, 0.9 mmol, 0.9 eq.) and IPA/H$_2$O (92.5/7.5%) (30.6% v/v based on DEAEMA/tBuMA) were placed into a 50 mL round-bottomed flask. The solution was stirred and deoxygenated using a nitrogen (N$_2$) purge for 15 minutes. Cu(I)Cl (42.8 mg, 0.4318 mmol, 1 eq.) was added to the flask and left to purge for a further 5 minutes. EBIB (84.2 mg, 0.4318 mmol, 1 eq.) was added to the flask under a positive flow of N$_2$, and the solution was left to polymerise at 40° C. Reactions were terminated when >99% conversion was reached, as judged by $^1$H NMR, by exposure to oxygen and addition of acetone. The catalyst residues were removed by passing the mixture over a basic alumina column. Acetone was removed under vacuum to concentrate the sample before precipitation into cold petroleum ether (40° C.-60° C.) and drying in the vacuum oven overnight.

1.6.3 Polymerisation of G2-DEAEMA$_x$Block-tBuMA$_y$

In a typical synthesis, targeting a DP$_n$=50 monomer units PDEAEMA$_{25}$-tBuMA$_{25}$; n$_{DEAEMA}$/n$_{Initiator}$: 50), bpy (134.9 mg, 0.8637 mmol, 2 eq.), DEAEMA (4 g, 21.59 mmol, 50 eq.) and IPA (38.9% v/v based on DEAEMA) were placed into a 50 mL round-bottomed flask. The solution was stirred and deoxygenated using a nitrogen (N$_2$) purge for 15 minutes. Cu(I)Cl (42.8 mg, 0.4318 mmol, 1 eq.) was added to the flask and left to purge for a further 5 minutes. G2-M (0.3934 mg, 0.4318 mmol, 1 eq.) was added to the flask under a positive flow of N$_2$, and the solution was left to polymerise at 40° C. The reaction was allowed to reach 80-90% conversion before tBuMA (1.5352, 10.80 mmol, 25 eq.), bpy (134.9 mg, 0.8637 mmol, 2 eq.) and Cu(I)Cl (42.8 mg, 0.4318 mmol, 1 eq.) dissolved in H$_2$O/IPA (92.5/7.5%) (27.3% v/v based on tBuMA) was added to the reaction mixture and left to polymerise overnight. Reactions were terminated when >99% conversion was reached, as judged by $^1$H NMR, by exposure to oxygen and addition of acetone. The catalyst residues were removed by passing the mixture over a basic alumina column. Acetone was removed under vacuum to concentrate the sample before precipitation into cold petroleum ether (40° C.-60° C.) and drying in the vacuum oven overnight.

1.6.4 Polymerisation of EBIB-DEAEMA$_x$-Block-tBuMA$_y$-EGDMA$_{0.9}$

In a typical synthesis, targeting a DP$_n$=50 monomer units PDEAEMA$_{25}$-tBuMA$_{25}$; n$_{DEAEMA}$/n$_{Initiator}$: 50), bpy (134.9 mg, 0.8637 mmol, 2 eq.), DEAEMA (4 g, 21.59 mmol, 50 eq.) and IPA (38.9% v/v based on DEAEMA) were placed into a 50 mL round-bottomed flask. The solution was stirred and deoxygenated using a nitrogen (N$_2$) purge for 15 minutes. Cu(I)Cl (42.8 mg, 0.4318 mmol, 1 eq.) was added to the flask and left to purge for a further 5 minutes. EBIB (84.2 mg, 0.4318 mmol, 1 eq.) was added to the flask under a positive flow of N$_2$, and the solution was left to polymerise at 40° C. The reaction was allowed to reach 80-90% conversion before tBuMA (1.5352, 10.80 mmol, 25 eq.), bpy (134.9 mg, 0.8637 mmol, 2 eq.), EGDMA (77 mg, 0.9 mmol, 0.9 eq.) and Cu(I)Cl (42.8 mg, 0.4318 mmol, 1 eq.) dissolved in H$_2$O/IPA (92.5/7.5%) (27.3% v/v based on tBuMA) was added to the reaction mixture and left to polymerise overnight. Reactions were terminated when >99% conversion was reached, as judged by $^1$H NMR, by exposure to oxygen and addition of acetone. The catalyst residues were removed by passing the mixture over a basic alumina column. Acetone was removed under vacuum to concentrate the sample before precipitation into cold petroleum ether (40° C.-60° C.) and drying in the vacuum oven overnight.

2. Polymerisation by ROP
2.1 ROP Dendron Initiator Synthesis
2.1.1 Synthesis of G1-pOH 2-(Dimethylamino)ethyl acrylate (6.0 g, 42 mmol, 6 eq.) was added to a 50 mL round 2 necked round-bottomed flask containing IPA (12 mL). The flask was deoxygenated under a positive N$_2$ purge for 10 minutes. Ethanolamine (0.4266 g, 6.9843 mmol, 1 eq.) dissolved in IPA (12 mL) was added drop wise while the solution was stirring in an ice bath under a positive flow of N$_2$. The final mixture was stirred for a further 10 minutes at 0° C. before being allowed to warm to room temperature and left stirring for 48 hrs. The solvent was removed and the product left to dry in vacuo overnight.

2.1.2 Synthesis of G2-pOH

CDI (39.137 g, 0.241 mol) was added to a 500 mL 2-neck RBF fitted with a reflux condenser, magnetic stirrer and a dry N$_2$ inlet. Dry toluene (350 mL) was added and the flask was purged with N$_2$ for 10 minutes. The solution was stirred at 60° C. and t-Butanol (35.7 g, 46 mL, 0.483 mol) was added via a warm syringe (Note: t-Butanol is a low melting solid, hence warm it in a water bath at 35° C. to allow it to melt to a liquid to easily get it out of the bottle by syringe). The mixture was left stirring at 60° C. for 6 hours under a positive flow of nitrogen. Following this, BAPA (16.077 g, 17.14 mL, 0.121 mol) was added dropwise whilst stirring and maintaining the temperature at 60° C. Upon addition, a white solid precipitate began to form in the flask (imidazole). The reaction was left stirring for a further 18 hours at 60° C. under a positive flow of nitrogen, and then allowed to cool to room temperature. The pale yellow solution was filtered to remove any solid imidazole, and concentrated in vacuo. The remaining oil was dissolved in dichloromethane (250 mL) washed with distilled water (3×250 mL) and finally a saturated brine solution (150 mL). The organic layer was dried with anhydrous Na$_2$SO$_4$, filtered and concentrated in vacuo to give G1-BAPA as a white solid powder. To remove any remaining residual solvents, the compound was placed under high vacuum overnight. (38 g, 95%). Found C, 57.84; H, 10.45; N, 12.91%. C$_{16}$H$_{33}$N$_3$O$_4$ requires, C, 57.98; H, 10.04; N, 12.68%. $^1$H NMR (400 MHz, CDCl$_3$) 5.19 (s, br, NH—disappears on addition of D$_2$O), 3.21 (t, 4H), 2.65 (t, 4H), 1.65 (q, 4H), 1.44 (s, 18H)$^{13}$C NMR (100 MHz, CDCl$_3$) 156.48, 79.34, 47.77, 39.29, 30.11, 28.79. m/z (ES MS) 332.3 [M+H]$^+$ A mixture of G1-BAPA (20 g, 0.06 mol) 16 mmol) in 1,4-dioxane (200 mL), bromoethanol (7.54 g, 0.6 mol), 30 mg of sodium iodide, and potassium carbonate (25.0 g, 1.8 mol) was refluxed overnight. After concentration of the reaction mixture, it was extracted with ethyl acetate (200 mL), washed with water (100 mL), dried over sodium sulfate, and filtered, and the solvent was removed under reduced pressure. Purification of the crude product by flash chromatography (2:1, ethyl acetate-hexane) produced G1-OH.

In a 1 L RBF, G1-OH (33.70 g) was dissolved in ethyl acetate (330 mL) and concentrated HCl (35.03 g, 30 mL, d=1.18 36% active) was added very slowly. CO$_2$ began to evolve. The reaction vessel was left open and stirring for 6 hours. The ethyl acetate was then removed in vacuo, and a crude $^1$H NMR (D$_2$O) of the remaining oil taken. The crude $^1$H NMR showed signs of incomplete decarboxylation (see page 7 for spectra), so the oil was re-dissolved in 250 mL ethyl acetate and heated to 55° C. for 5 hours. After removal of ethyl acetate, the crude oil was dissolved in 4M NaOH (300 mL), and then reduced down by half (approx.) on the rotary evaporator (60° C.). Following this, the oily mixture was extracted twice with CHCl$_3$ (300 mL). The organic layers were then combined, dried with anhydrous $Na_2SO_4$, filtered and concentrated in vacuo to give bis(3-aminopropyl)amino)propanol as a pale yellow oil.

2-(Dimethylamino)ethyl acrylate (6.0 g, 42 mmol, 6 eq.) was added to a 50 mL round 2 necked round-bottomed flask containing IPA (12 mL). The flask was deoxygenated under a positive $N_2$ purge for 10 minutes. Bis(3-aminopropyl) amino)propanol (1.2271 g, 6.984 mmol, 1 eq.) dissolved in IPA (12 mL) was added drop wise while the solution was stirring in an ice bath under a positive flow of $N_2$. The final mixture was stirred for a further 10 minutes at 0° C., allowed to warm to room temperature and left stirring for 48 hrs. The solvent was removed and the product left to dry in vacuo overnight.

2.2 Synthesis of Bifunctional Caprolactone 2.2.2 Synthesis of 4,4'-Bioxepanyl-7,7'-Dione (BOD)

Urea hydrogen peroxide ($CO(NH_2).H_2O_2$) (20 g, 0.21 mol) was added to a 500 mL round-bottom flask containing formic acid (100 mL). The solution was stirred for 2 h at room temperature. The flask was then immersed in an ice bath to control the exotherm resulting from the following stage of the procedure. Bicyclohexanone (10 g, 0.05 mol) was slowly added to the solution over a period of 5-10 min. The reaction mixture was stirred for 4 h whilst the ice bath was changed periodically. 200 mL of water was then added to the mixture followed by extraction with chloroform (200 mL×4). The organic fraction was collected and washed with a saturated aqueous sodium bicarbonate solution then dried overnight with $Na_2SO_4$. After removing the solvent under reduced pressure, a white powder was isolated and analysed by NMR and compared to the literature reported values.

2.3 Polymerisation by ROP 2.3.1 Ring Opening Polymerisation of ε-Caprolactone

The typical protocol for the homopolymerisation of CL for a target number average degree of polymerization DP=50 was as follows. A 50 mL single necked round bottomed flask was purged with nitrogen for 15 minutes. $SnOct_2$ catalyst (0.0018 g, 0.0044 mmol) was added by syringe and needle and the flask purged further. Distilled CL (3.773 g, 3.5 mL, 33.06 mmol) was introduced into a 50 mL flask and the flask purged for a further 10 minutes. Anhydrous G1pOH (0.2316 g, 0.6666 mmol) was added via syringe. The flask was then immersed in a preheated oil bath at 110° C. and vigorously stirred for the required reaction time of ~20 hours. The reaction was killed by submerging the reaction in an ice bath and the polymer purified by dissolving in THF and precipitating into hexane.

2.3.2 Ring Opening Polymerisation of ε-Caprolactone and 4,4'-Bioxepanyl-7,7'-Dione (PCL-BOD)

The typical protocol for the homopolymerisation of CL for a target number average degree of polymerization DP=50 was as follows. A 50 mL single necked round bottomed flask containing BOD (0.9183 g 4.059 mmol) was purged with nitrogen for 15 minutes. $SnOct_2$ catalyst (0.0079 g, 0.0195 mmol) was added by syringe and needle and the flask purged further. Distilled CL (23.28 g, 21.6 mL, 204 mmol) was introduced into a 50 mL flask and the flask purged for a further 10 minutes. Anhydrous BzOH (0.7315 g, 0.7 mL, 6.764 mmol) was added via syringe. The flask was then immersed in a preheated oil bath at 110° C. and vigorously stirred for the required reaction time of ~20 hours. The reaction was killed by submerging the reaction in an ice bath and the polymer purified by dissolving in THF and precipitating into hexane.

In Vitro Cell Viability Experiments

The effect of nanoparticles carrying SN38, in accordance with the present invention, on the viability of murine CT-26 cells, was investigated. It was found that, whilst SN38 is responsible for a reduction in cell viability, the nanoparticle carrier itself does not affect cell viability.

The following polymer compositions (mixtures of branched polymers and block copolymers) were used:

JF1: $p(HPMA_{50}$-co-$EGDMA_{0.9})$:$p(PEG_{114}$-b-$HPMA_{120})$ 50:50 wt %

JF2: $p(nBuMA_{50}$-co-$EGDMA_{0.8})$:$p(PEG_{114}$-b-$HPMA_{120})$ 50:50 wt %

JF3: $p(tBuMA_{25}$-co-$HPMA_{25}$-co-$EGDMA_{0.9})$:$p(PEG_{114}$-b-$HPMA_{120})$ 50:50 wt %

The following protocol was followed.

Nanoparticle Samples—5 wt % Encapsulation of SN-38

1. Add 30 uL of sample (JF1-3) to 970 uL media (final concentration is 4 uM)
2. Add 15 uL of sample (JF1-3) to 970 uL media and 15 uL water (final concentration is 2 uM)
3. Add 7.5 uL of sample (JF1-3) to 970 uL media and 22.5 uL water (final concentration is 1 uM)

For SN38 in DMSO

1. Make 2.5 mM stock SN38 solution (2 mg in 2000 uL DMSO)
2. Add 1.6 uL of stock to 968.4 uL media and then add 30 uL sterile water (final concentration is 4 uM)
3. Add 2 uL of stock to 2 ul of DMSO (serial dilution of 1:2), add 1.6 uL of this to 968.4 uL media and 30 uL sterile water (final concentration is 2 uM)
4. Add 2 uL of previous intermediate stock to 2 uL DMSO (serial dilution of 1:2), add 1.6 uL of this to 968.4 uL media and 30 uL sterile water (final concentration is 1 uM)

For Controls

1. Add 1.6 uL DMSO to 968.4 uL media and then add 30 uL sterile water
2. Add 30 uL sterile water to 970 uL media For Blanks 1. Add 30 uL of sample (B1-3) to 970 uL media (final concentration is 4 uM)
2. Add 15 uL of sample (B1-3) to 970 uL media and 15 uL water (final concentration is 2 uM)
3. Add 7.5 uL of sample (B1-3) to 970 uL media and 22.5 uL water (final concentration is 1 uM)

Aspirate media on 96 well plate and dose with 100 uL of each solution in triplicate followed by detection with a 96 well plate reader, absorbance 490 nm.

Figure 20:
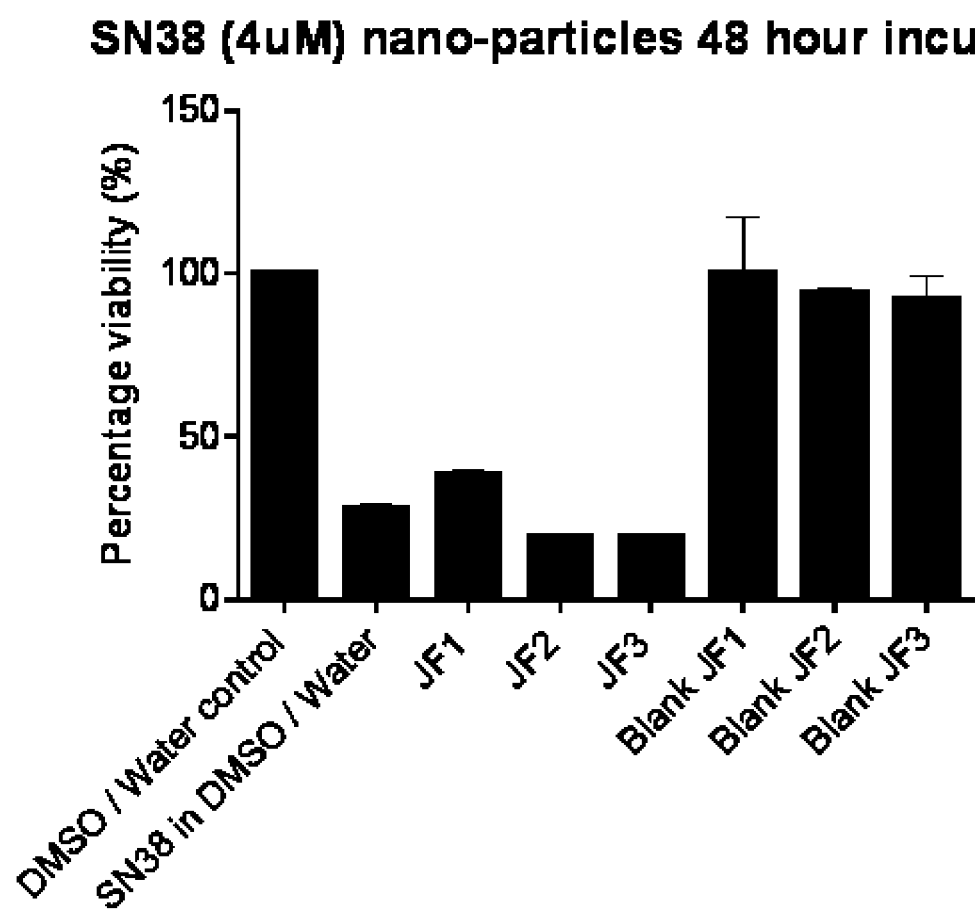
FIG. 20 shows the effect on cell viability of some nanoparticles of the present invention.

As shown in FIG. 20, after a 48 hour incubation period, the 5 wt % SN38 encapsulated nanoparticles samples, and the SN38 in DMSO/water sample, resulted in reduced cell viability (approximately 25% to 45%, compared to 100% for the control). In contrast, the blank samples (i.e. those containing the polymeric constituents of the nanoparticles but not the SN38) resulted in 100% cell viability, within error margins.

What is claimed is:

1. Particles comprising both a branched polymer and a linear dendritic hybrid, wherein said branched polymer and said linear dendritic hybrid are not covalently bonded to one another, and wherein said branched polymer is not a linear dendritic hybrid and the particles are obtained by co-precipitation, and wherein the linear dendritic hybrid comprises dendrons comprising amine groups and a linear polymer chain which is a vinyl polymer and the branched polymer is a branched vinyl polymer.

2. Particles as claimed in claim 1 wherein the vinyl polymer comprises hydroxypropyl methacrylate (HPMA), n-butyl methacrylate (nBuMA), t-butyl methacrylate (tBuMA), N,N-diethylaminoethyl methacrylate (DEAEMA) or styrene.

3. Particles as claimed in claim 1 wherein the branched vinyl polymer comprises one or more of the monomers HPMA, nBuMA, tBuMA, styrene, and DEAEMA.

4. Particles as claimed in claim 1 wherein the branched vinyl polymer comprises a brancher selected from ethylene glycol dimethacrylate (EGDMA) and 1,4-butanediol di(methacryloyloxy)-ethyl ether (BDME).

5. Particles as claimed in claim 1 further comprising a drug, prodrug or other biologically active component.

6. Particles as claimed in claim 5 wherein the drug is an HIV antiretroviral, anticancer drug, or ibuprofen.

7. Particles as claimed in claim 1 which are nanoparticles.

8. Particles as claimed in claim 1 in solid form.

9. A composition containing particles as claimed in claim 1 dispersed in water or an aqueous phase.

10. A method of drug delivery comprising administering a therapeutically effective amount of the particles of claim 5 to a patient, wherein said particles comprise a drug, prodrug or other biologically active component.

11. A method of treating HIV or cancer comprising administering a therapeutically effective amount of the particles of claim 5 to a patient in need thereof, wherein said particles further comprise an HIV antiretroviral or anticancer drug, respectively.

12. A method of preparing particles as defined in claim 1 comprising:
dissolving the branched polymer and linear dendritic hybrid copolymer, and optionally other component(s), in a solvent to form a solution;
adding said solution to a different liquid;
removing said solvent to form a dispersion of co-precipitated particles; and
optionally further replicating the following steps, one or more times:
adding further solution (of the branched polymer and the linear dendritic hybrid, and optionally the other component(s), in the solvent) to the liquid; and
removing the solvent.

* * * * *